US012694518B2

(12) United States Patent
Epstein et al.

(10) Patent No.: US 12,694,518 B2
(45) Date of Patent: Jul. 28, 2026

(54) INTRAMYOCARDIAL TISSUE DISPLACEMENT AND MOTION MEASUREMENT AND STRAIN ANALYSIS FROM MRI CINE IMAGES USING DENSE DEEP LEARNING

(71) Applicant: UNIVERSITY OF VIRGINIA PATENT FOUNDATION, Charlottesville, VA (US)

(72) Inventors: Frederick H. Epstein, Charlottesville, VA (US); Changyu Sun, Charlottesville, VA (US); Sona Qadimi, Charlottesville, VA (US); Yu Wang, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 208 days.

(21) Appl. No.: 18/277,500

(22) PCT Filed: Feb. 2, 2022

(86) PCT No.: PCT/US2022/014903
§ 371 (c)(1),
(2) Date: Aug. 16, 2023

(87) PCT Pub. No.: WO2022/177741
PCT Pub. Date: Aug. 25, 2022

(65) Prior Publication Data
US 2024/0046464 A1 Feb. 8, 2024

Related U.S. Application Data

(60) Provisional application No. 63/149,900, filed on Feb. 16, 2021.

(51) Int. Cl.
G06T 7/00 (2017.01)
G01R 33/56 (2006.01)
(Continued)

(52) U.S. Cl.
CPC .............. G06T 7/0012 (2013.01); G06T 3/40 (2013.01); G06T 7/246 (2017.01); G16H 50/20 (2018.01);
(Continued)

(58) Field of Classification Search
CPC ......... G06T 7/0012; G06T 3/40; G06T 7/246; G06T 2207/10081; G06T 2207/10088;
(Continued)

(56) References Cited

U.S. PATENT DOCUMENTS 7,813,537 B2 10/2010 Epstein et al.
8,700,127 B2 4/2014 Salerno et al.
(Continued)

FOREIGN PATENT DOCUMENTS

CN 111012377 A * 4/2020 ........... A61B 8/0883

OTHER PUBLICATIONS

Lehmonen Lauri: "Quantification of MRI-derived myocardial motion in specified cardiac disorders", Doctoral School in Natural Sciences Dissertation Series, Nov. 25, 2020 (Nov. 25, 2020), XP055967799, Retrieved from the Internet <URL:https://helda.helsinki.fi/bitstream/handle/10138/321148/lehmonen_lauri_dissertation_2020.pdf?sequence=1&isAllowed=y> [retrieved on 20221004].
(Continued)

*Primary Examiner* — Amandeep Saini
*Assistant Examiner* — Andrew S Budisalich
(74) *Attorney, Agent, or Firm* — Meunier Carlin & Curfman LLC

(57) ABSTRACT
An exemplary method and system are disclosed that employ DENSE deep learning neural-network(s) trained with dis-
(Continued)

placement-encoded imaging data (i.e., DENSE data) to estimate intramyocardial motion from cine MRI images and other cardiac medical imaging modalities, including standard cardiac computer tomography (CT) images, magnetic resonance imaging (MRI) images, echocardiogram images, heart ultrasound images, among other medical imaging modalities described herein. The DENSE deep learning neural-network(s) can be configured (trained) using (i) contour motion data from displacement-encoded imaging magnitude data as inputs to the neural network and (ii) displacement maps derived from displacement-encoded imaging phase images for comparison to the outputs of the neural network for neural network adjustments during the training.

20 Claims, 18 Drawing Sheets

(51) Int. Cl.
| | | |
|---|---|---|
| G06T 3/40 | (2024.01) | |
| G06T 7/246 | (2017.01) | |
| G16H 50/20 | (2018.01) | |

(52) U.S. Cl.
CPC .............. *G06T 2207/10081* (2013.01); *G06T 2207/10088* (2013.01); *G06T 2207/20084* (2013.01); *G06T 2207/30048* (2013.01)

(58) Field of Classification Search
CPC . G06T 2207/20084; G06T 2207/30048; G06T 7/0016; G06T 7/248; G06T 2207/10016; G06T 2207/10081; G16H 50/20; G01R 33/5608; G01R 33/56316; G01R 33/56325
See application file for complete search history.

(56) References Cited

U.S. PATENT DOCUMENTS

| | | | | |
|---|---|---|---|---|
| 9,183,626 | B2 | 11/2015 | Zhao et al. | |
| 9,224,210 | B2 | 12/2015 | Epstein et al. | |
| 9,589,345 | B2 | 3/2017 | Zhao et al. | |
| 9,953,439 | B2 | 4/2018 | Salerno et al. | |
| 10,143,384 | B2 | 12/2018 | Chen et al. | |
| 10,310,047 | B2 | 6/2019 | Cai et al. | |
| 10,830,855 | B2 | 11/2020 | Cai et al. | |
| 2008/0015428 | A1* | 1/2008 | Epstein | G06T 7/215 |
| | | | | 600/410 |
| 2011/0133736 | A1 | 6/2011 | Zhong | |
| 2012/0134595 | A1* | 5/2012 | Fonseca | G06T 3/40 |
| | | | | 382/298 |
| 2015/0099964 | A1 | 4/2015 | Voigt et al. | |
| 2019/0302210 | A1 | 10/2019 | Epstein et al. | |
| 2020/0249306 | A1 | 8/2020 | Abdishektaei et al. | |
| 2020/0363485 | A1 | 11/2020 | Sun et al. | |
| 2021/0219862 | A1* | 7/2021 | Loecher | G06N 3/045 |
| 2021/0267455 | A1 | 9/2021 | Ghadimi et al. | |

OTHER PUBLICATIONS

Spottiswoode, B.S. ; Zhong, X. ; Lorenz, C.H. ; Mayosi, B.M. ; Meintjes, E.M. ; Epstein, F.H.: "Motion- guided segmentation for cine DENSE MRI", Medical Image Analysis, Oxford University Press, Oxofrd, GB, vol. 13, No. 1, Feb. 1, 2009 (Feb. 1, 2009), GB , pp. 105-115, XP025746116, ISSN: 1361-8415, DOI: 10.1016/j.media.2008.06.016.

Edward Ferdian; Avan Suinesiaputra; Kenneth Fung; Nay Aung; Elena Lukaschuk; Ahmet Barutcu; Edd Maclean; Jose Paiva; Stefan K. Pie: "Fully Automated Myocardial Strain Estimation from CMR Tagged Images using a Deep Learning Framework in the UK Biobank", arxiv.org, Cornell University Library, 201 Olin Library Cornell University Ithaca, NY 14853, Apr. 15, 2020 (Apr. 15, 2020), 201 Olin Library Cornell University Ithaca, NY 14853 , XP081644840, DOI: 10.1148/ryct.2020190032.

Ghadimi Sona, Auger Daniel A., Feng Xue, Sun Changyu, Meyer Craig H., Bilchick Kenneth C., Cao Jie Jane, Scott Andrew D., Oshinski: "Fully-automated global and segmental strain analysis of DENSE cardiovascular magnetic resonance using deep learning for segmentation and phase unwrapping", Journal of Cardiovascular Magnetic Resonance, vol. 23, No. 1, Dec. 1, 2021 (Dec. 1, 2021), XP055967761, DOI: 10.1186/s12968-021-00712-9.

Kar Julia, Zhong X, MV Cohen, DA Cornejo, et al.: "Introduction to a mechanism for automated myocardium boundary detection with displacement encoding with stimulated echoes (DeNSe)", British Institute of Radiology, Jan. 1, 2018 (Jan. 1, 2018), XP055967753, [retrieved on Oct. 4, 2022].

International Search Report and Written Opinion issued for Application No. PCT/US2022/014903, dated Apr. 6, 2022.

Amzulescu, et al., "Myocardial Strain Imaging: Review of General Principles, Validation, and Sources of Discrepancies", European Heart Journal—Cardiovascular Imaging, vol. 20, No. 6, pp. 605-619, Jun. 2019.

Baker, et al., "A Database and Evaluation Methodology for Optical Flow", International Journal of Computer Vision, vol. 92, pp. 1-31, Nov. 30, 2010.

Bilchick, et al., "CMR DENSE and the Seattle Heart Failure Model Inform Survival and Arrhythmia Risk After CRT", JACC: Cardiovascular Imaging, vol. 13, No. 4, pp. 924-936, Apr. 2020.

Buss, et al., "Assessment of Myocardial Deformation with Cardiac Magnetic Resonance Strain Imaging Improves Risk Stratification in Patients with Dilated Cardiomyopathy", European Heart Journal—Cardiovascular Imaging, vol. 16, No. 3, pp. 307-315, Mar. 2015.

Drafts, et al., "Low to Moderate Dose Anthracycline-Based Chemotherapy Is Associated with Early Noninvasive Imaging Evidence of Subclinical Cardiovascular Disease", JACC: Cardiovascular Imaging, vol. 6, No. 8, pp. 877-885, Aug. 2013.

Gilliam, et al., "Automated Motion Estimation for 2-D Cine DENSE MRI", IEEE Transactions on Medical Imaging, vol. 31, No. 9, pp. 1669-1681, Sep. 2012.

Horn , et al., "Determining Optical Flow", Proceedings, vol. 0281, Techniques and Applications of Image Understanding, pp. 185-203, Nov. 12, 1981.

Ilg, et al., "FlowNet 2.0: Evolution of Optical Flow Estimation with Deep Networks", IEEE Conference on Computer Vision and Pattern Recognition (CVPR), pp. 1-16, 2017.

Ji, et al., "3D Convolutional Neural Networks for Human Action Recognition", IEEE Transactions on Pattern Analysis and Machine Intelligence, vol. 35, No. 1, pp. 221-231, Mar. 6, 2012.

Kim, et al., "Myocardial Tissue Tracking with Two-Dimensional Cine Displacement-Encoded MR Imaging: Development and Initial Evaluation", Radiological Society of North America, vol. 230, No. 3, pp. 862-871, Mar. 2004.

Lin, et al., "Reproducibility of Cine Displacement Encoding with Stimulated Echoes (DENSE) in Human Subjects", Magnetic Resonance Imaging, vol. 35, pp. 148-153, Jan. 1, 2017.

Lindman, et al., "Management of Asymptomatic Severe Aortic Stenosis: Evolving Concepts in Timing of Valve Replacement", JACC: Cardiovascular Imaging, vol. 13, No. 2, Part 1, pp. 481-493, Feb. 2020.

Mangion, et al., "Circumferential Strain Predicts Major Adverse Cardiovascular Events Following an Acute ST-Segment-Elevation Myocardial Infarction", Radiology, vol. 290, No. 2, pp. 329-337, Feb. 2019.

Mangion, et al., "Displacement Encoding With Stimulated Echoes Enables the Identification of Infarct Transmurality Early Postmyocardial Infarction", Journal of Magnetic Resonance Imaging, vol. 52, No. 6, pp. 1722-1731, Dec. 2020.

Ong, et al., "Myocardial Strain Imaging by Cardiac Magnetic Resonance for Detection of Subclinical Myocardial Dysfunction in Breast Cancer Patients Receiving Trastuzumab and Chemotherapy", International Journal of Cardiology, vol. 261, pp. 228-233, Jun. 15, 2018.

(56)  References Cited

OTHER PUBLICATIONS

Pedrizzetti, et al., "Principles of Cardiovascular Magnetic Resonance Feature Tracking and Echocardiographic Speckle Tracking for Informed Clinical Use", Journal of Cardiovascular Magnetic Resonance, vol. 18, No. 1, pp. 1-12, Jan. 6, 2016.

Plana, et al., "Expert Consensus for Multimodality Imaging Evaluation of Adult Patients During and After Cancer Therapy: A Report from the American Society of Echocardiography and the European Association of Cardiovascular Imaging", European Heart Journal—Cardiovascular Imaging, vol. 15, No. 10, pp. 1063-1093, Oct. 2014.

Ronneberger, et al., "U-Net: Convolutional Networks for Biomedical Image Segmentation", International Conference on Medical Image Computing and Computer-Assisted Intervention, pp. 234-241, Nov. 18, 2015.

Scatteia, et al., "Strain Imaging Using Cardiac Magnetic Resonance", Heart Failure Reviews, vol. 22, pp. 465-476, Jun. 15, 2017.

Schuster, et al., "Cardiovascular Magnetic Resonance Myocardial Feature Tracking: Concepts and Clinical Applications", Advances in Cardiovascular Imaging, vol. 9, No. 4, pp. 1-9, Mar. 23, 2016.

Shetty, et al., "Cardiac Magnetic Resonance-Derived Anatomy, Scar, and Dyssynchrony Fused with Fluoroscopy to Guide LV Lead Placement in Cardiac Resynchronization Therapy: A Comparison with Acute Haemodynamic Measures and Echocardiographic Reverse Remodelling", European Heart Journal—Cardiovascular Imaging, vol. 14, No. 7, pp. 692-699, Jul. 2013.

Simpson, et al., "MR Assessment of Regional Myocardial Mechanics", Journal of Magnetic Resonance Imaging, vol. 37, No. 3, pp. 576-599, Mar. 2013.

Spottiswoode, et al., "Motion-Guided Segmentation for Cine DENSE MRI", Medical Image Analysis, vol. 13, No. 1, pp. 105-115, Feb. 2009.

Spottiswoode, et al., "Tracking Myocardial Motion from Cine DENSE Images Using Spatiotemporal Phase Unwrapping and Temporal Fitting", IEEE Transactions on Medical Imaging, vol. 26, No. 1, pp. 15-30, Jan. 2007.

Szymanski, et al., "Should LVEF Be Replaced by Global Longitudinal Strain?", Hearts, vol. 100, No. 21, pp. 1655-1656, Nov. 2014.

Tayal, et al., "The Feasibility of a Novel Limited Field of View Spiral Cine DENSE Sequence to Assess Myocardial Strain in Dilated Cardiomyopathy", Magnetic Resonance Materials in Physics, Biology and Medicine, vol. 32, No. 3, pp. 317-329, Jan. 29, 2019.

Tran, et al., "Learning Spatiotemporal Features with 3D Convolutional Networks", International Conference on Computer Vision, pp. 4489-4497, Feb. 17, 2015.

Wehner, et al., "Comparison of Left Ventricular Strains and Torsion Derived from Feature Tracking and DENSE CMR", Journal of Cardiovascular Magnetic Resonance, vol. 20, No. 63, pp. 1-11, Feb. 7, 2018.

Xu, et al., "A Region-Growing Algorithm for InSAR Phase Unwrapping", IEEE Transactions on Geoscience and Remote Sensing, vol. 37, No. 1, pp. 124-134, Jan. 31, 1999.

Young, et al., "Generalized Spatiotemporal Myocardial Strain Analysis for DENSE and SPAMM Imaging", Magnetic Resonance in Medicine, vol. 67, No. 6, pp. 1590-1599, Jun. 2012.

Zhong, et al., "Imaging Three-Dimensional Myocardial Mechanics Using Navigator—Gated Volumetric Spiral Cine DENSE MRI", Magnetic Resonance in Medicine, vol. 64, No. 4, pp. 1089-1097, Oct. 2010.

* cited by examiner

*300a*

| |
|---|
| Retrieve a medical image scan of a subject 302 |

↓

| |
|---|
| Determine intramyocardial motion data in the medical image scan using a trained neural network 304 |

FIG. 3A

*300b*

| |
|---|
| Acquire a plurality of cine DENSE MRI scan 306 |

↓

| |
|---|
| Determine (i) displacement encoded magnitude data and (ii) displacement encoded phase data from the acquired cine DENSE MRI 308 |

↓

| |
|---|
| Determine contours of the displacement encoded magnitude data 310 |

↓

| |
|---|
| Determine displacement map of the displacement encoded phase data 312 |

↓

| |
|---|
| Train a neural network using the contours of the displacement encoded magnitude data as inputs to the neural network and adjust configuration of the neural network using the displacement map of the displacement encoded phase data 314 |

FIG. 3B

300c

Retrieve a medical image scan of a subject

*302*

Determine intramyocardial motion data in the medical image
scan using a trained neural network

*304*

Output the determined intramyocardial motion data in the
medical image scan (e.g., for diagnosis or treatment of disease)

300d

Retrieve a medical image scan of a subject

*302*

Determine intramyocardial motion data in the medical image
scan using a trained neural network

*304*

Determine strain-associated data of myocardium or wall using
the determined intramyocardial motion data

*318*

Output the strain-associated data and/or intramyocardial motion
data (e.g., for diagnosis or treatment of disease)

INTRAMYOCARDIAL TISSUE DISPLACEMENT AND MOTION MEASUREMENT AND STRAIN ANALYSIS FROM MRI CINE IMAGES USING DENSE DEEP LEARNING

CROSS-REFERENCE TO RELATED APPLICATION

This Application is a National Stage of International Application No. PCT/US2022/014903 filed Feb. 2, 2022, which claims priority to and the benefit under 35 U.S.C § 119(e) of U.S. Provisional Patent Application Ser. No. 63/149,900, entitled "System and Method for Improved Cardiac MRI Feature Tracking by Learning from Displacement-Encoded Imaging," filed Feb. 16, 2021, each of which is hereby incorporated by reference herein in its entirety as if fully set forth below.

GOVERNMENT LICENSE RIGHTS

This invention was made with government support under grant no. R01HL147104 awarded by the National Institute of Health. The government has certain rights in the invention.

TECHNICAL FIELD

This disclosure relates to the measurement of intramyocardial tissue displacement and motion from biomedical images using a neural network trained using displacement-encoded imaging measurements.

BACKGROUND

Cardiac magnetic resonance (CMR) myocardial strain imaging can provide measurements of intramyocardial tissue displacement and motion that can be used to determine physical properties of the heart tissue such as strain, strain rate, torsion, twist, among others. These intramyocardial motions and strain measurements can beneficially be employed in the diagnostics, as well as prognostic, of various heart diseases such as cardiotoxicity due to anti-cancer therapy, coronary heart disease, heart valve problems, inflammatory conditions such as pericarditis, cardiac tumors, or scarring, and other damage from a heart attack.

CMR myocardial strain imaging techniques such as Displacement-ENcoding with Stimulated Echoes (DENSE) and other methods such as myocardial tagging can directly measure intramyocardial tissue displacement, but additional scans are needed, thereby lengthening the overall CMR examination time. In a DENSE acquisition, tissue displacement is encoded into the MRI phase images to allow for the quantification of intramyocardial displacement and the subsequent computation of myocardial strain. The technique is highly sensitive and accurate and is generally employed in research but has not been widely accepted for use in the clinical diagnostics of heart disease due to the associated cost of increased examination time.

To provide strain imaging or estimation of intramyocardial motion from standard cine MRI scans, post-processing techniques such as feature tracking (or "tissue tracking") may be used that generally entails tracking myocardial borders in cine MRI videos. It, however, lacks the same degree of accuracy as compared to dedicated strain imaging techniques such as displacement-encoded imaging. Cine images are short movies that show heart motion throughout the cardiac cycle.

There is a benefit to improving the accuracy of displacement and strain analysis of standard cine MRI images and/or augmenting the measuring of intramyocardial motion in other cardiac medical imaging modalities.

SUMMARY

An exemplary method and system are disclosed that employ deep neural-network(s) trained with displacement-encoded imaging data (i.e., DENSE data) to estimate intramyocardial motion from cine MRI images and other cardiac medical imaging modalities, including standard cardiac computer tomography (CT) images, magnetic resonance imaging (MRI) images, echocardiogram images, and heart ultrasound images, among other medical imaging modalities described herein. The DENSE deep learning neural-network(s) may be configured (trained) using (i) contour motion data from displacement-encoded imaging magnitude data as inputs to the neural network and (ii) displacement maps derived from displacement-encoded imaging phase images for comparison to the outputs of the neural network for neural network adjustments during the training. The training can create a correspondence, via these adjustments and provided training set, between (i) the contour motion and (ii) the displacement map, each provided from the provided displacement-encoded imaging images, to provide a trained neural network that is configured to output a displacement map or displacement data corresponding to or indicating, the intramyocardial motion from a subsequent input of cine MRI images or other 4D biomedical imaging scans (as well as 2D images+time or 3D images+time). From the estimated displacement map or displacement data, an analysis system can determine strain, strain rate, torsion, twist data that can be outputted to be employed by clinicians or researchers in the diagnostics of cardiac disease or conditions.

The trained neural network has wide applications to other biomedical imaging scans and can be employed to provide or augment the analysis of intramyocardial motion and associated strain, strain rate, torsion, twist, activation-time data of these other 4D biomedical imaging scans and associated techniques. Though trained via displacement-encoded MRI images, the trained neural network through the noted trained correspondence between (i) the contour motion and (ii) the displacement map can be configurable to operate on various spatial resolutions and temporal frames of 4D biomedical imaging scans. In some embodiments, the 4D biomedical imaging scans can be adjusted in their spatial resolutions and temporal frames to match the DENSE MRI images. In other embodiments, the displacement-encoded MRI training data set can be adjusted in spatial resolutions and temporal frames to match that of another 4D biomedical imaging scans to provide a trained neural network that is particularly tailored for that image type.

A study was performed to evaluate DENSE-trained deep learning neural networks. The study observed that DENSE-trained deep learning neural networks can estimate intramyocardial motion from contour motion, show good agreement with displacement-encoded imaging ground truth, and outperform a commercial feature tracking algorithm for global and segmental circumferential strain.

In an aspect, a method is disclosed of determining intramyocardial motion and/or measurand (e.g., strain, twist, and torsion) in medical image scans, the method comprising retrieving, by a processor, a medical image scan of a subject; determining, by the processor, intramyocardial motion data in the medical image scan, in part, using a trained neural network, wherein the trained neural network has been trained by (i) generating a set of contour motion images or data from Displacement-ENcoding with Stimulated Echoes (DENSE) magnitude images or data and (ii) a set of displacement map image or data from the DENSE phase image or data; and (ii) configuring a neural network comprising an input and output to generate the trained neural network by (a) applying the set of contour motion images or data to the input to generate an output displacement map image or data and (ii) applying the displacement map image or data to the output displacement map to adjusts weights of the neural network, wherein the determined intramyocardial motion data, or a parameter derived therefrom, is outputted in a report or employed in a control operation for the diagnostics or treatment of cardiac disease or cardiac health-related conditions.

In some embodiments, the medical image scan is at least one of cardiac computer tomography (CT) images, magnetic resonance imaging (MRI) images, echocardiogram images, heart ultrasound images).

In some embodiments, the method further includes determining, by the processor, a set of values associated with at least one of a strain parameter, a strain rate parameter, a torsion parameter, and a twist parameter using the determined intramyocardial motion data, wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

In some embodiments, the set of contour motion images or data is generated by binarizing pixels of the DENSE magnitude images or data to a binary value corresponding to contour motions defined within the DENSE magnitude images or data.

In some embodiments, the set of contour motion images or data is further generated by scaling the DENSE magnitude images or data to pre-defined image size; and cropping the scaled DENSE magnitude images or data to an image region of interest.

In some embodiments, the neural network comprises a convolutional neural network comprising one or more convolution layers, one or more batch normalization layers, one or more ReLU layers, and one or more pooling layers, the layers being connected collectively to form a network.

In some embodiments, the neural network comprises a 3D UNet neural network.

In some embodiments, the DENSE magnitude images or data and the DENSE phase image or data are determined from a plurality of DENSE training data sets, wherein the plurality of DENSE training data sets are acquired by: acquiring first data comprising a stimulated echo and a Tl relaxation echo; acquiring second data comprised of a second stimulated echo, a second Tl relaxation echo, and a second stimulated anti-echo; acquiring at least one of original frames comprising the stimulated echo and the Tl relaxation echo; acquiring at least one of additional original frames comprising a stimulated echo, a Tl relaxation echo, and a stimulated anti-echo; and acquiring a plurality of new original frames of displacement encoded stimulated echo (DENSE) cine frames of MRI image data of a subject.

In another aspect, a method is disclosed of training a neural network to generate an output displacement map corresponding to intramyocardial motion in a biomedical image, the method comprising generating a set of contour motion images or data from DENSE magnitude images or data; generating a set of displacement map image or data from DENSE phase image or data; and adjusting weights of the neural network by (i) applying the set of contour motion images or data to the input of the neural network to generate an output displacement map image or data and (ii) using a loss function determined using the displacement map image or data and the output displacement map in a loss function, wherein the determined intramyocardial motion data, or a parameter derived therefrom, is outputted in a report or employed in a control operation for the diagnostics or treatment of cardiac disease or cardiac health-related conditions.

In some embodiments, the medical image scan is at least one of cardiac computer tomography (CT) images, magnetic resonance imaging (MRI) images, echocardiogram images, heart ultrasound images).

In some embodiments, the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

In some embodiments, the set of contour motion images or data is generated by: scaling the DENSE magnitude images or data to pre-defined image size; cropping the scaled DENSE magnitude images or data to an image region of interest; and binarizing pixels of the DENSE magnitude images or data to a binary value corresponding to contour motions defined within the DENSE magnitude images or data.

In some embodiments, the neural network comprises a 3D UNet neural network.

In some embodiments, the DENSE magnitude images or data and the DENSE phase image or data are determined from a plurality of DENSE training data sets, wherein each of the DENSE training data sets is acquired by: acquiring first data comprising a stimulated echo and a Tl relaxation echo; acquiring second data comprised of a second stimulated echo, a second Tl relaxation echo, and a second stimulated anti-echo; acquiring at least one of original frames comprising the stimulated echo and the Tl relaxation echo; acquiring at least one of additional original frames comprising a stimulated echo, a Tl relaxation echo, and a stimulated anti-echo; and acquiring a plurality of new original frames of displacement encoded stimulated echo (DENSE) cine frames of MRI image data of a subject.

A system is disclosed comprising a processor; and a memory having instructions stored thereon to determine intramyocardial motion and/or measurand (e.g., strain, twist, and torsion) in medical image scans, wherein execution of the instructions by the processor causes the processor to: retrieve medical image scan of a subject; determine intramyocardial motion data in the medical image scan, in part, using a trained neural network, wherein the trained neural network has been trained by (i) generating a set of contour motion images or data from DENSE magnitude images or data and (ii) a set of displacement map image or data from the DENSE phase image or data; and (ii) configuring a neural network comprising an input and output to generate the trained neural network by (a) applying the set of contour motion images or data to the input to generate an output displacement map image or data and (ii) applying the displacement map image or data to the output displacement map to adjusts weights of the neural network, wherein the determined intramyocardial motion data, or a parameter derived therefrom, is outputted in a report or employed in a control operation for the diagnostics or treatment of cardiac disease or cardiac health-related conditions.

In some embodiments, the medical image scan is at least one of cardiac computer tomography (CT) images, magnetic resonance imaging (MRI) images, echocardiogram images, heart ultrasound images).

In some embodiments, the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

In some embodiments, the instructions include a first instruction to scale the DENSE magnitude images or data to pre-defined image size; a second instruction to crop the scaled DENSE magnitude images or data to an image region of interest; and a third instruction to binarize pixels of the DENSE magnitude images or data to a binary value corresponding to contour motions defined within the DENSE magnitude images or data.

In another aspect, a non-transitory computer-readable medium is disclosed having instructions stored thereon to determine intramyocardial motion and/or measurand (e.g., strain, twist, and torsion) in medical image scans, wherein execution of the instructions by the processor causes the processor to retrieve medical image scan of a subject; determine intramyocardial motion data in the medical image scan, in part, using a trained neural network, wherein the trained neural network has been trained by (i) generating a set of contour motion images or data from DENSE magnitude images or data and (ii) a set of displacement map image or data from the DENSE phase image or data; and (ii) configuring a neural network comprising an input and output to generate the trained neural network by (a) applying the set of contour motion images or data to the input to generate an output displacement map image or data and (ii) applying the displacement map image or data to the output displacement map to adjusts weights of the neural network, wherein the determined intramyocardial motion data, or a parameter derived therefrom, is outputted in a report or employed in a control operation for the diagnostics or treatment of cardiac disease or cardiac health-related conditions.

In some embodiments, the medical image scan is at least one of cardiac computer tomography (CT) images, magnetic resonance imaging (MRI) images, echocardiogram images, heart ultrasound images).

In some embodiments, the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

In some embodiments, the instructions include a first instruction to scale the DENSE magnitude images or data to pre-defined image size; a second instruction to crop the scaled DENSE magnitude images or data to an image region of interest; and a third instruction to binarize pixels of the DENSE magnitude images or data to a binary value corresponding to contour motions defined within the DENSE magnitude images or data.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

The trained neural network may be used to determine intramyocardial motion data, or a parameter derived therefrom (e.g., strain, strain rate, torsion, twist, activation time), for the diagnostics or treatment of cardiac disease or cardiac health-related conditions such as, but not limited to, coronary heart disease, heart valve problems, inflammatory conditions such as pericarditis, cardiac tumors, scarring and other damage from a heart attack, or for cardiac resynchronization therapy. DENSE images acquired of other parts of the body (of the head or brain) may be similarly used to train a neural network, e.g., for the diagnostics or treatment of brain-related disease or conditions such as, but not limited to, Parkinson's disease, tremor, epilepsy, neurodegenerative conditions or diseases, Alzheimer's, seizures, paralysis, or psychiatric disease.

Other aspects and features, according to the example embodiments of the disclosed technology, will become apparent to those of ordinary skill in the art upon reviewing the following detailed description in conjunction with the accompanying figures.

BRIEF DESCRIPTION OF THE DRAWINGS

FIG. 3A shows a method of using a DENSE neural network in accordance with an illustrative embodiment.

FIG. 3B shows a method of training a DENSE neural network in accordance with an illustrative embodiment.

FIG. 3C shows another method of using a DENSE neural network in accordance with an illustrative embodiment.

FIG. 3D shows yet another method of using a DENSE neural network in accordance with an illustrative embodiment.

DETAILED DESCRIPTION

Figure 1:
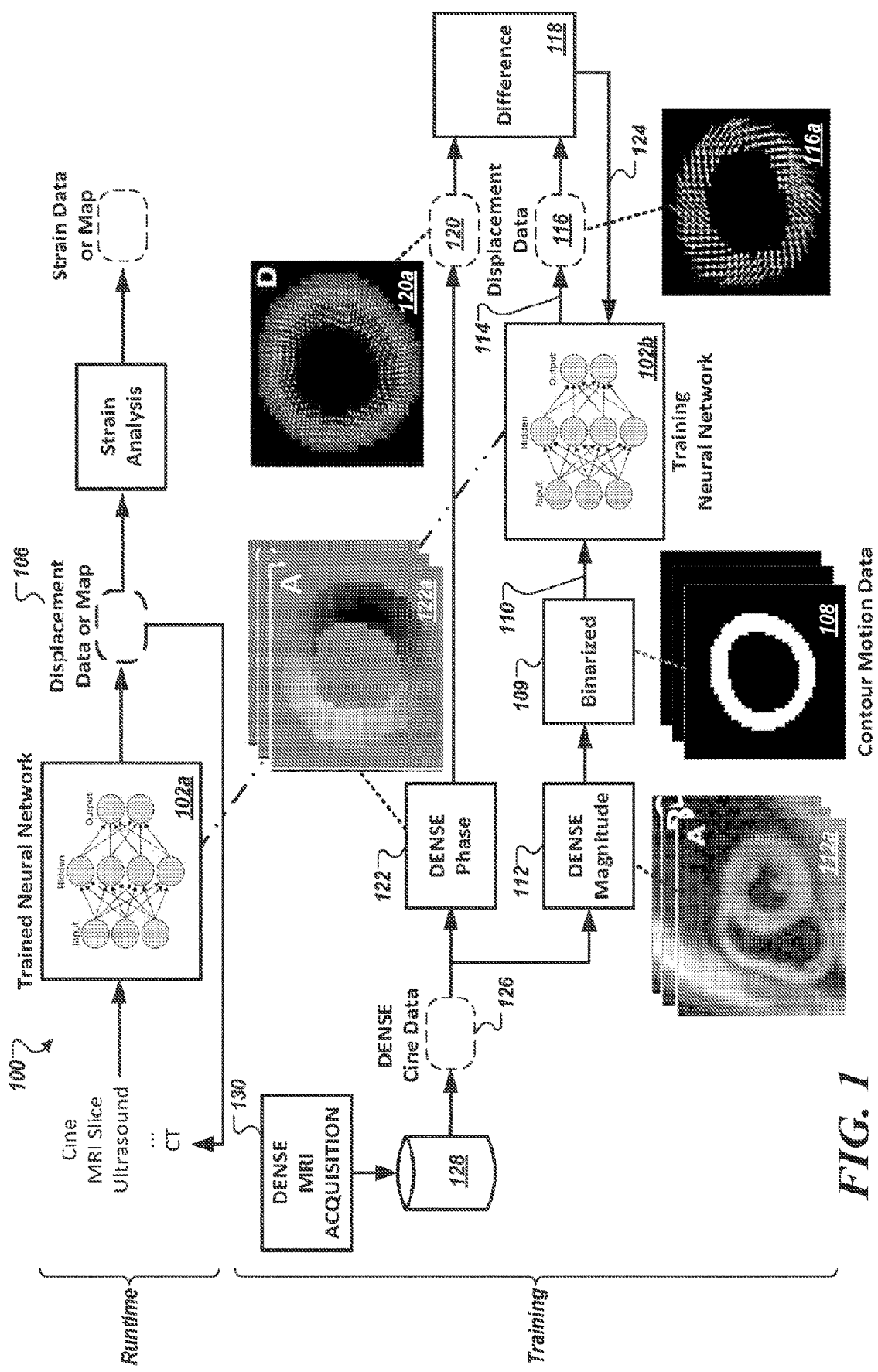
FIG. 1 is a system diagram illustrating an operating environment capable of implementing aspects of the present disclosure of determining intramyocardial motion and/or measurand (e.g., strain, twist, and torsion) in medical image scans using a DENSE MRI training data set in accordance with an illustrative embodiment.

In some aspects, the disclosed technology relates to free-breathing parameter mapping with high-contrast image registration. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organisms, living or dead, or other biological or molecular structure or chemical environment, and may relate to particular components of the subject, for instance, specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [6] refers to the 6th reference in the list, namely Scatteia, A., Baritussio, A. & Bucciarelli-Ducci, C, "Strain imaging using cardiac magnetic resonance," Heart Fail Rev 22, 465-476 (2017). All references cited and discussed in this specification are incorporated herein by reference in their entireties and to the same extent as if each reference was individually incorporated by reference.

In the following description, references are made to the accompanying drawings that form a part hereof and that show, by way of illustration, specific embodiments or examples. In referring to the drawings, like numerals represent like elements throughout the several figures.

FIG. 1 is a system diagram illustrating an operating environment 100 capable of implementing aspects of the present disclosure of determining intramyocardial motion and/or measurand (e.g., strain, twist, torsion, activation time) in medical image scans using a DENSE MRI training data set in accordance with an illustrative embodiment. In the example shown in FIG. 1, the system comprising a trained neural network 102 (shown as 102a) is configured to generate, from provided biomedical images or videos 104 (shown as "Cine, MRI slice, Ultrasound, . . . , CT" 104), displacement-encoded data 106, e.g., a displacement map, that provides an estimation of intramyocardial motion in the provided biomedical images 104. The intramyocardial motion data 106 may be overlaid over the input biomedical images or videos 104. The intramyocardial motion data 106 can be analyzed, e.g., via a strain analysis 107, or other analyses, to determine strain, strain rate, torsion, twist, activation time, among others.

In the example shown in FIG. 1, the neural network 102 (shown as 102b) has been trained (i.e., configured) to have a correspondence between (i) the contour motion from an input displacement encoded image training data set (e.g., DENSE data set) and (ii) an output displacement encoded data indicating the intramyocardial motion of a subject. Examples of these biomedical images to which intramyocardial motion can be ascertained and overlaid include, and without being limiting, cardiac computer tomography (CT) images, magnetic resonance imaging (MRI) images, echocardiogram images, heart ultrasound images.

To create this correspondence between the contour motion data and the displacement data, the neural network 102b is trained using a sequence of contour motion data 108 as its input 110 in which the contour motion data 108 is derived from displacement encoded magnitude data 112 (shown as "DENSE magnitude" data 112). The contour motion data 108 is generated from a binary operator 109 configured to binarize as well as scale and/or crop the displacement encoded magnitude data 112. The neural network 102b outputs 114 displacement data 116 (shown as 116a) that are then compared (shown as "Difference" module 118) to the ground-truth displacement data 120 (shown as 120a) derived from displacement encoded phase data 122 (shown as "DENSE phase" data 122). The comparison (e.g., via a subtraction operator or a SoftMax operator) can generate feedback 124 to adjust the weights of the neural network 102b. Example images of the displacement encoded magnitude data 112 and displacement encoded phase data 122 are shown as 112a and 122a, respectively. The displacement encoded magnitude data (e.g., 112, 112a) and phase data (e.g., 122, 122a) can be generated from cine DENSE data 126 retrieved from a data store 128 and having been acquired through DENSE MRI acquisition 130, e.g., as described in U.S. Patent Publication no. 20190302210, which is incorporated by reference in its entirety.

Example Method of Operation

The DENSE-trained deep learning neural network and associated method can operate with an imaging modality of any spatial resolution and any temporal frames.

Figure 2A:
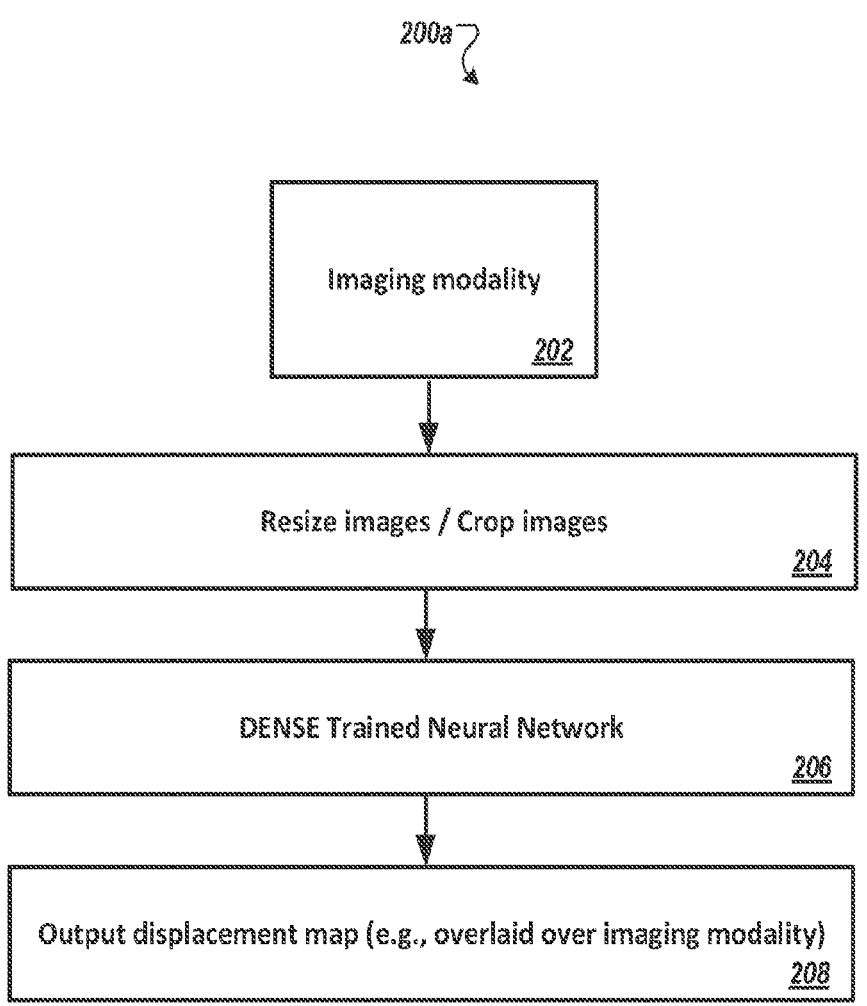
FIG. 2A shows an example method of using a DENSE-trained deep learning neural network for a given imaging modality in accordance with an illustrative embodiment.

FIG. 2A shows an example method 200a of using a DENSE-trained deep learning neural network for a given imaging modality in accordance with an illustrative embodiment. In FIG. 2A, a set of time-series images are acquired 202 from an imaging modality such as cardiac computer tomography (CT) images, magnetic resonance imaging (MRI) images, echocardiogram images, or heart ultrasound images. The acquired images are resized (204) as pre-processed images to match the size of the trained data set of the trained neural network (e.g., 102a, 102b) and cropped to a region of interest. The pre-processed images provided (206) as input to the trained neural network can then provide a displacement map. The displacement map can be outputted (208) to be used for the diagnostics or the treatment of cardiac disease or the cardiac health-related conditions.

Figure 2B:
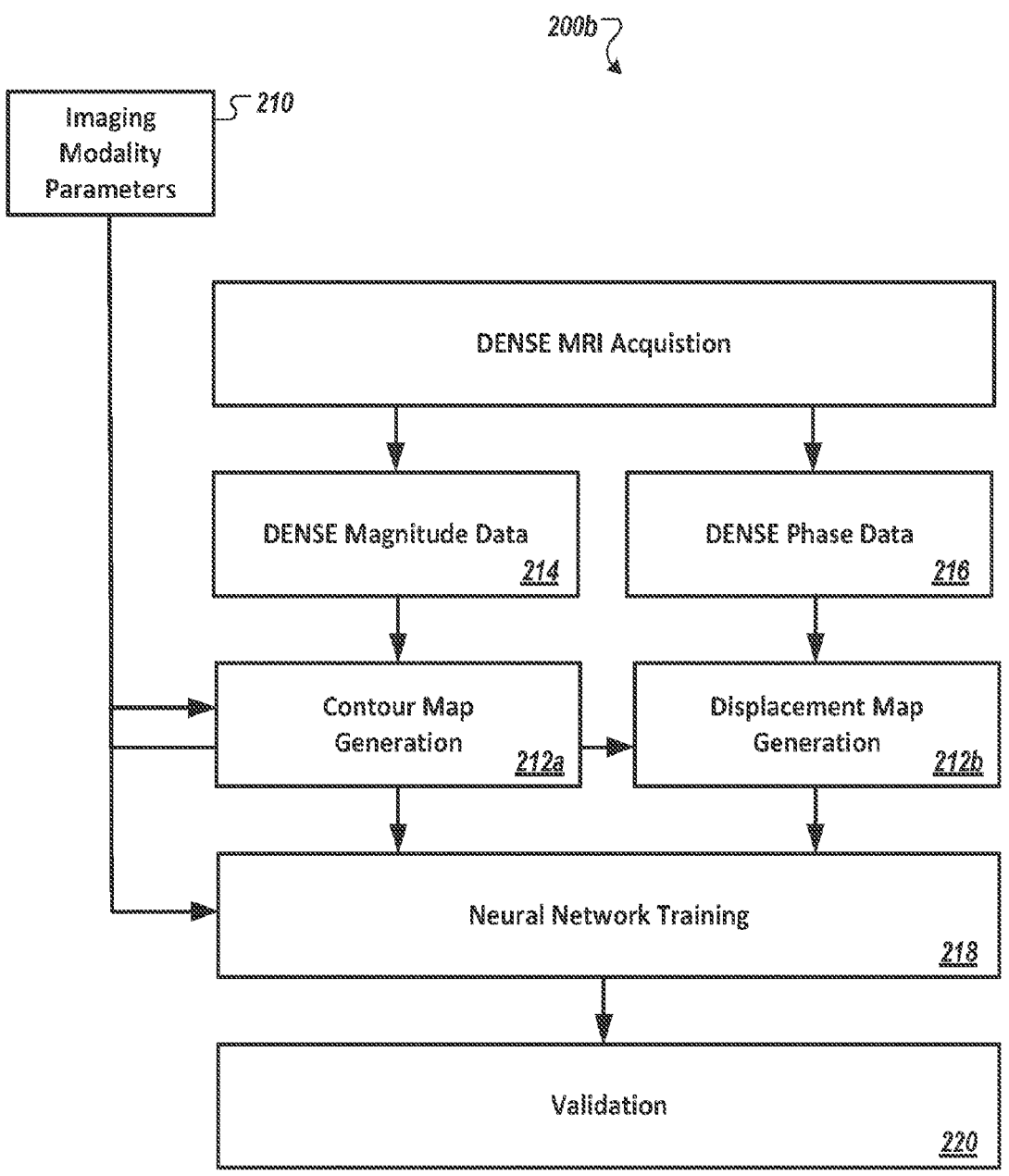
FIG. 2B shows an example method of using a DENSE-trained deep learning neural network for a given imaging modality in accordance with an illustrative embodiment.

FIG. 2B shows an example method 200b of using a DENSE-trained deep learning neural network for a given imaging modality.

Conventional MRI technology discussed herein is discussed in 20190302210, which is incorporated by reference in its entirety as if set forth fully herein. Phase-contrast displacement encoding that has been used for myocardial imaging and cine DENSE (Displacement Encoding with Stimulated Echoes) imaging have emerged as a strain imaging technique that can offer high spatial resolution, equivalent accuracy, better reproducibility, and where strain analysis is less time-consuming. DENSE can also provide quantification of numerous features from myocardial tissue, where tissue displacement is encoded as a phase of a stimulated-echo signal (STE). In an embodiment, a method includes acquiring magnetic resonance data associated with physiological activity in an area of interest of a subject, where the acquired magnetic resonance data includes one or more phase-encoded data sets. The operation may include acquiring frames comprising a stimulated echo, a T1 relaxation echo, and a stimulated anti-echo. The method, configured in software, determines, from at least one or more phase-encoded data sets, an output data set (e.g., displacement-encoded information) corresponding to the physiological activity in the area of interest. Reconstruction of the images includes performing phase unwrapping of the phase-encoded data set using region growing along multiple pathways based on phase predictions.

MRI imaging encompasses techniques such as the acquisition of "cine images." Cine images are short movies that can show heart motion throughout the cardiac cycle in short-axis. For example, measurement of left ventricular (LV) mass, ejection fraction, percentage of LV mass subtended by scar, and extracellular volume may be some of the heart tissue qualities studied with cine data. Cine DENSE, therefore, measures myocardial displacements by encoding tissue displacement into the signal phase. Displacement encoding frequencies ($k_e$) are selected to balance signal-to-noise ratio, displacement sensitivity, and artifact suppression, resulting in phase wrapping during systole.

Spatio-temporal phase unwrapping is required to compute Lagrangian motion trajectories and strain. Phase unwrapping may be aided by delineating the myocardium using myocardial contours. Displacement encoding with stimulated echoes (DENSE), therefore, may be described as tools that measure myocardial displacements using the signal phase.

In FIG. 2B, the DENSE training data set are modified to match that of an imaging modality of interest. The parameters of an imaging modality are determined (210), such as size. The image parameters are used to adjust (shown as 212a, 212b) the image size of the training set of the contour data objects (e.g., 108) and the displacement data (e.g., 120). As previously discussed, the contour data object (e.g., 108) are generated (214) from DENSE magnitude data, and the displacement data (e.g., 120) are generated (216) from DENSE phase data. The neural network is trained (218) using the contour data (from step 212a) and displacement map (from step 212b). Following training, the neural network is validated (220). Once trained, the neural network can be used to determine intramyocardial tissue displacement and motion from other imaging modalities having a similar image size. The process of FIG. 2B can be used in combination with the process of FIG. 2A.

Per FIGS. 2A and 2B, while most methods of operations are limited to fixed image size or have to be cut to specific temporal frames, the exemplary method of use or training can handle the spatial resolution of various imaging modalities by resizing those images. And for the temporal frames, the exemplary method can accept any length of frames. This robust operation allows the exemplary method to be applied to a broader range of images.

FIGS. 3A-3E each shows an example method of operation of using and/or training a DENSE neural network in accordance with an illustrative embodiment.

Method of Using a DENSE Neural Network

FIG. 3A shows a method 300a of using a DENSE neural network in accordance with an illustrative embodiment. The method 300a includes retrieving (302) a medical image scan of a subject. A set of time-series images are acquired from an imaging modality such as cardiac computer tomography (CT) images, magnetic resonance imaging (MRI) images, echocardiogram images, or heart ultrasound images.

The method 300a then includes determining (304) intramyocardial motion data in the medical image scan using a trained neural network, e.g., trained according to the description of FIG. 1 or FIG. 3B.

Method of Training a DENSE Neural Network

FIG. 3B shows a method 300b of training a DENSE neural network in accordance with an illustrative embodiment. The method 300b includes acquiring (306) a plurality of cine DENSE MRI scan. Example method of acquiring the DENSE MRI scan is described in U.S. Patent Publication no. 20190302210, which is incorporated by reference in its entirety.

The method 300b then includes determining (308) (i) displacement encoded magnitude data and (ii) displacement encoded phase data from the acquired cine DENSE MRI. Example method such determination is also provided in U.S. Patent Publication no. 20190302210 or US20200249306.

The method 300b then includes determining (310) contours (e.g., contour object data) of the displacement encoded magnitude data. In some embodiments, segmentation of LV myocardium may be performed semiautomatically using motion-guided segmentation, and manual correction was applied if needed. Example method of determining the contour data in the DENSE MRI scan is described in U.S. Patent Publication no. 20190302210.

The method 300b then includes determining (312) displacement map (e.g., displacement object data) of the displacement encoded phase data.

The method 300b then includes training (314) a neural network using the contour object data of the displacement encoded magnitude data as inputs to the neural network and adjusting configuration of the neural network using the displacement map object data of the displacement encoded phase data, e.g., as described in relation to FIG. 1. An example training may involve using multi-fold cross-validation. The neural network may be trained using an Adam optimizer configured to execute a pre-defined number of epochs (e.g., 100-500 epochs) or until training criteria are met. The training used the end-point-error based on cross-entropy or mean squared error, among others, as the loss function.

Another Method of Using a DENSE Neural Network

FIG. 3C shows a method 300c of using a DENSE neural network in accordance with an illustrative embodiment. The method 300c includes retrieving (302) a medical image scan of a subject, e.g., as described in FIG. 3A. A set of time-series images are acquired from an imaging modality such as cardiac computer tomography (CT) images, magnetic resonance imaging (MRI) images, echocardiogram images, or heart ultrasound images.

The method 300c then includes determining (304) intramyocardial motion data in the medical image scan using a trained neural network, e.g., trained according to the description of FIG. 1 or FIG. 3B.

The method 300c then includes outputting (306) the determined intramyocardial motion data in the medical image scan (e.g., for diagnosis or treatment of disease). The output may include intramyocardial motion data for the diagnostics or treatment of cardiac disease or cardiac health-related conditions such as, but not limited to, coronary heart disease, heart valve problems, inflammatory conditions such as pericarditis, cardiac tumors, scarring, and other damage from a heart attack, or for cardiac resynchronization therapy. DENSE images acquired of other parts of the body (of the head or brain) may be similarly used to train a neural network, e.g., for the diagnostics or treatment of brain-related disease or conditions such as, but not limited to, Parkinson's disease, tremor, epilepsy, neurodegenerative conditions or diseases, Alzheimer's, seizures, paralysis, or psychiatric disease.

Another Method of Using a DENSE Neural Network

FIG. 3D shows a method 300d of using a DENSE neural network in accordance with an illustrative embodiment. The method 300d includes retrieving (302) a medical image scan of a subject, e.g., as described in FIG. 3A, 3C. A set of time-series images are acquired from an imaging modality such as cardiac computer tomography (CT) images, magnetic resonance imaging (MRI) images, echocardiogram images, or heart ultrasound images.

The method 300d then includes determining (304) intramyocardial motion data in the medical image scan using a trained neural network, e.g., trained according to the description of FIG. 1 or FIG. 3B. The method 300d then includes determining (318) strain-associated data of myocardium or wall using the determined intramyocardial motion data.

Strain data can be determined from the intramyocardial motion data per Equation 1.

$$e = \frac{1}{2}\left[\nabla_x u + (\nabla_x u)^T\right] + \frac{1}{2}\left[(\nabla_x u)^T \times (\nabla_x u)\right] \quad \text{(Eq. 1)}$$

where $$u(x) = u(x, y, z) = \begin{bmatrix} u_x \\ u_y \\ u_z \end{bmatrix} \text{ and } \nabla_x u = \begin{pmatrix} \dfrac{\partial u_x}{\partial x} & \dfrac{\partial u_x}{\partial y} & \dfrac{\partial u_x}{\partial z} \\ \dfrac{\partial u_y}{\partial x} & \dfrac{\partial u_y}{\partial y} & \dfrac{\partial u_y}{\partial z} \\ \dfrac{\partial u_z}{\partial x} & \dfrac{\partial u_z}{\partial y} & \dfrac{\partial u_z}{\partial z} \end{pmatrix}$$

Lagrangian strain between each neighboring landmark can be calculated for each sub-segment as $\varepsilon_{Long} = (L - L_0)L_0 \times 100\%$ where $L_0$ is the Euclidean distance between neighboring landmarks, at the first frame.

Strain rate may be determined from intramyocardial motion data per Equation 2.

$$\epsilon'_{P_l, P_k} = V_{P_k, x} - V_{P_l, x}/L_{P_l, P_k} \quad \text{(Eq. 2)}$$

where $P_k$ and $P_l$ are points on a curve representing a myocardial muscle volume sample.

The method 300d then includes outputting (320) the strain-associated data and/or the determined intramyocardial motion data in the medical image scan (e.g., for diagnosis or treatment of disease). The output (320) can include intramyocardial motion data and/or strain, strain rate, torsion, twist, activation time, to be used for the diagnostics or treatment of cardiac disease or cardiac health-related conditions such as, but not limited to, coronary heart disease, heart valve problems, inflammatory conditions such as pericarditis, cardiac tumors, scarring and other damage from a heart attack, or for cardiac resynchronization therapy. DENSE images acquired of other parts of the body (of the head or brain) may be similarly used to train a neural network, e.g., for the diagnostics or treatment of brain-related disease or conditions such as, but not limited to, Parkinson's disease, tremor, epilepsy, neurodegenerative conditions or diseases, Alzheimer's, seizures, paralysis, or psychiatric disease.

Another Method of Using a DENSE Neural Network

Figure 3E:
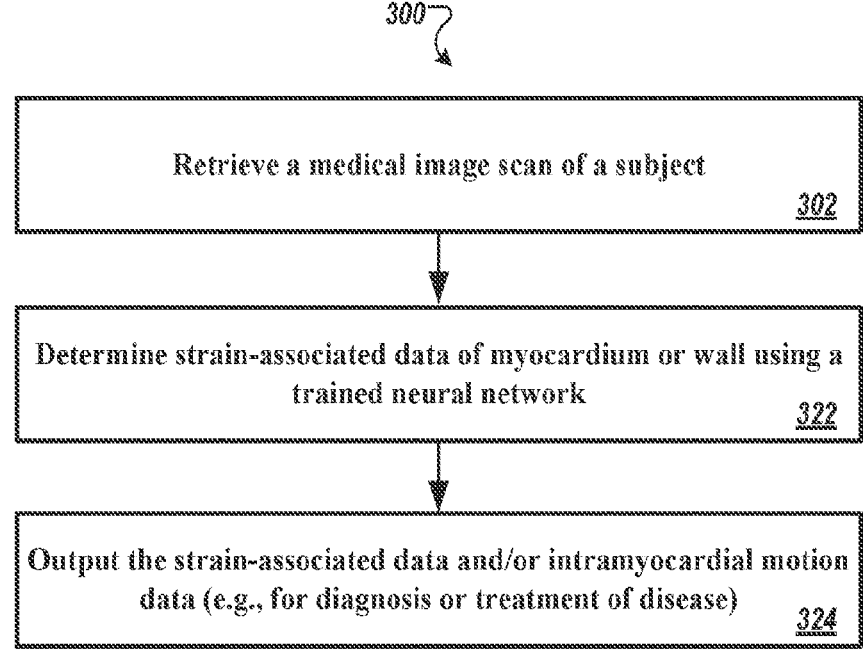
FIG. 3E shows yet another method of using and training a DENSE neural network in accordance with an illustrative embodiment.

FIG. 3E shows a method 300e of using a DENSE neural network in accordance with an illustrative embodiment. The method 300e includes retrieving (302) a medical image scan of a subject, e.g., as described in FIG. 3A, 3C. A set of time-series images are acquired from an imaging modality such as cardiac computer tomography (CT) images, magnetic resonance imaging (MRI) images, echocardiogram images, or heart ultrasound images.

The method 300d then includes determining (304) strain-associated data of myocardium or wall using a trained neural network. The trained neural network may be configured by training the neural network using contour data in conjunction with strain, strain rate, torsion, twist, activation time derived from DENSE displacement data. Similar to other examples described herein, the neural network is trained using as its inputs the contour object data. However, rather than using the DENSE displacement data as ground truth, the DENSE displacement data, e.g., from DENSE phase-encoded data, can be used to calculate strain, strain rate, torsion, twist, activation time that is used, e.g., in a loss function of the neural network.

The method 300e then includes outputting (324) the determined strain-associated data for the diagnostics or treatment of cardiac disease or cardiac health-related conditions such as, but not limited to, coronary heart disease, heart valve problems, inflammatory conditions such as pericarditis, cardiac tumors, scarring and other damage from a heart attack, or for cardiac resynchronization therapy. DENSE images acquired of other parts of the body (of the head or brain) may be similarly used to train a neural network, e.g., for the diagnostics or treatment of brain-related disease or conditions such as, but not limited to, Parkinson's disease, tremor, epilepsy, neurodegenerative conditions or diseases, Alzheimer's, seizures, paralysis, or psychiatric disease.

Results

Example Implementations and Results

Figure 5A:
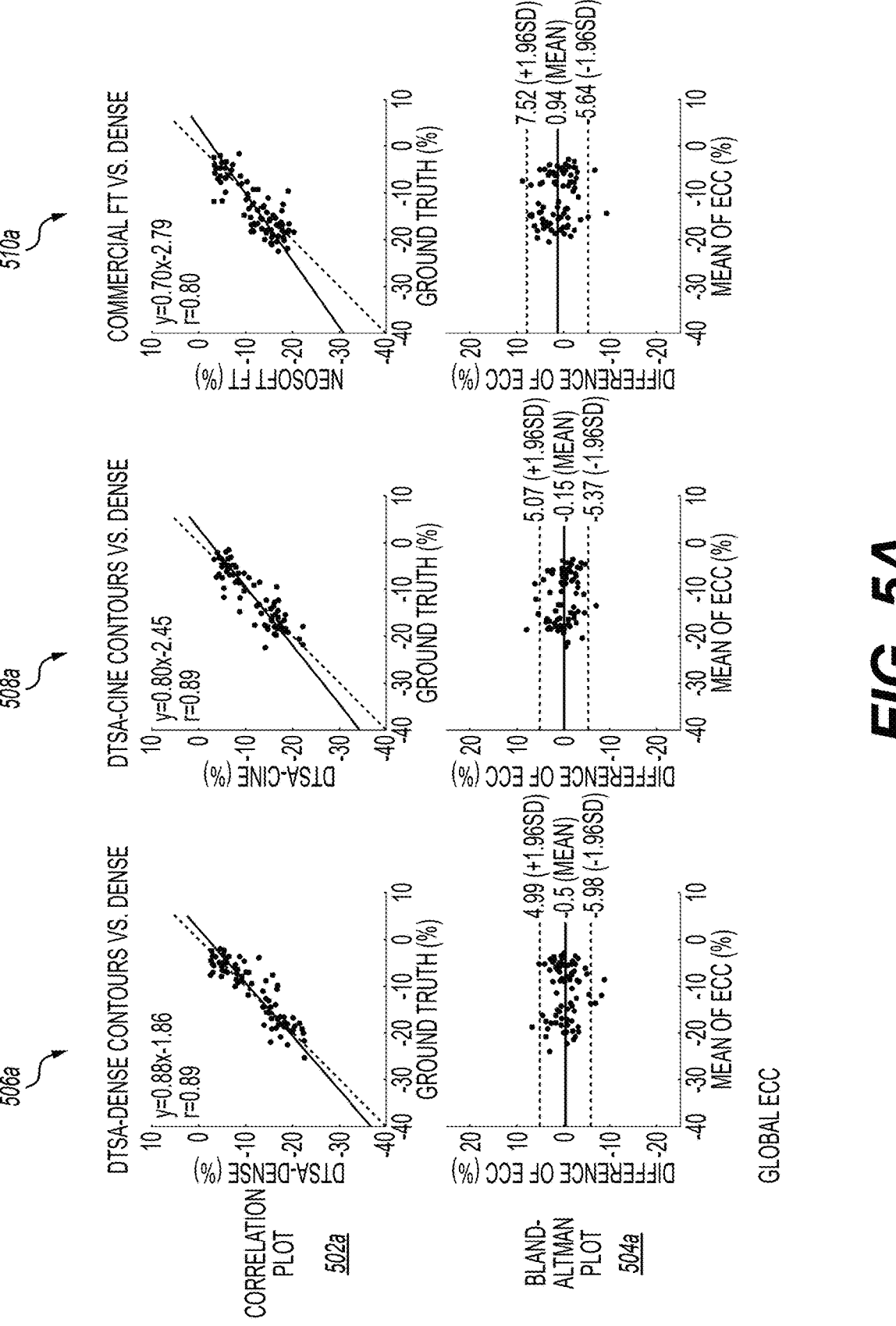
FIGS. 5A and 5B, respectively, show correlation plots and Bland-Altman plots in the estimation of global $E_{cc}$ and segmental $E_{cc}$ data using the DENSE contour data objects and the cine contour data objects in accordance with an illustrative embodiment.
Figure 5B:
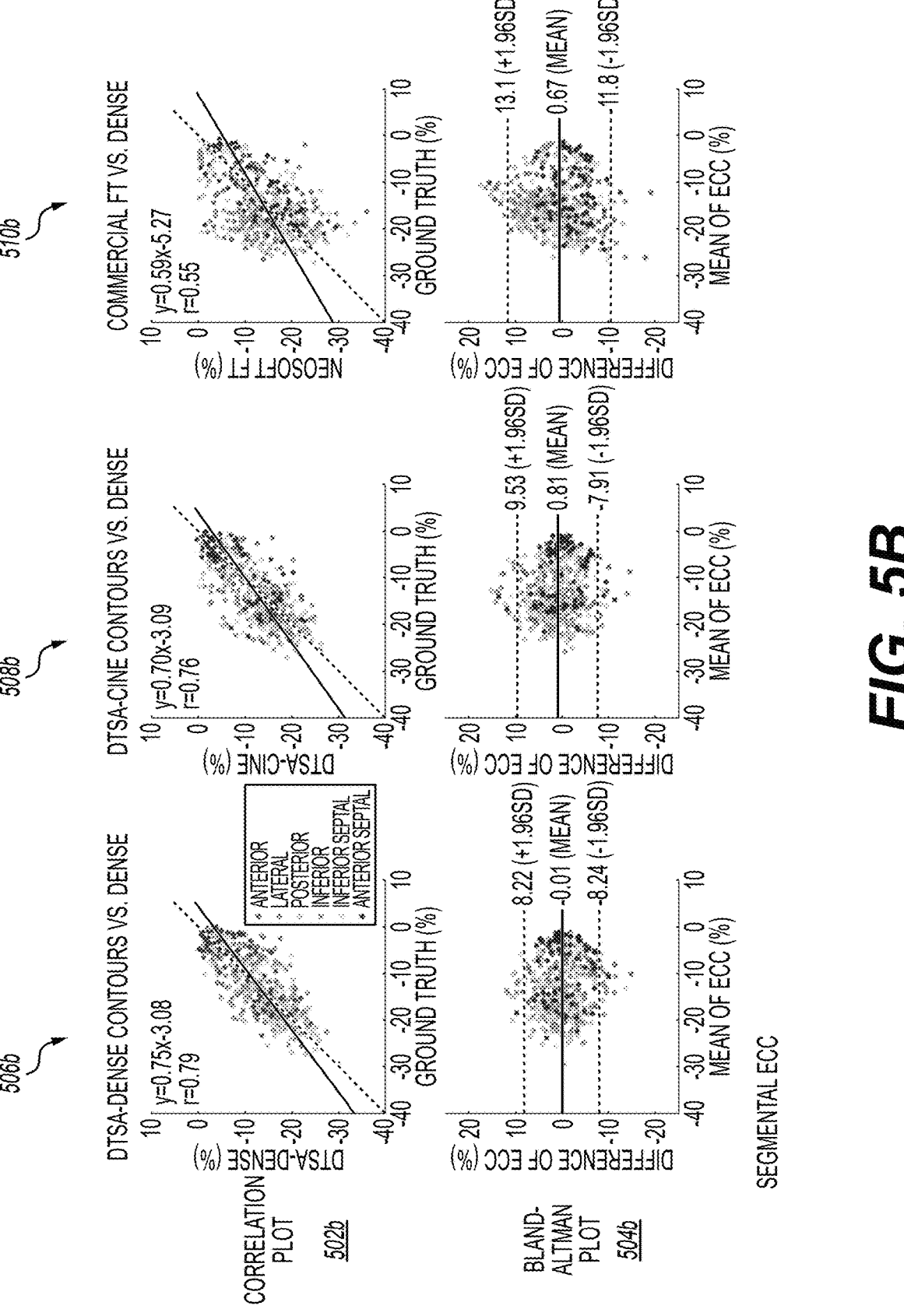
Figure 6:
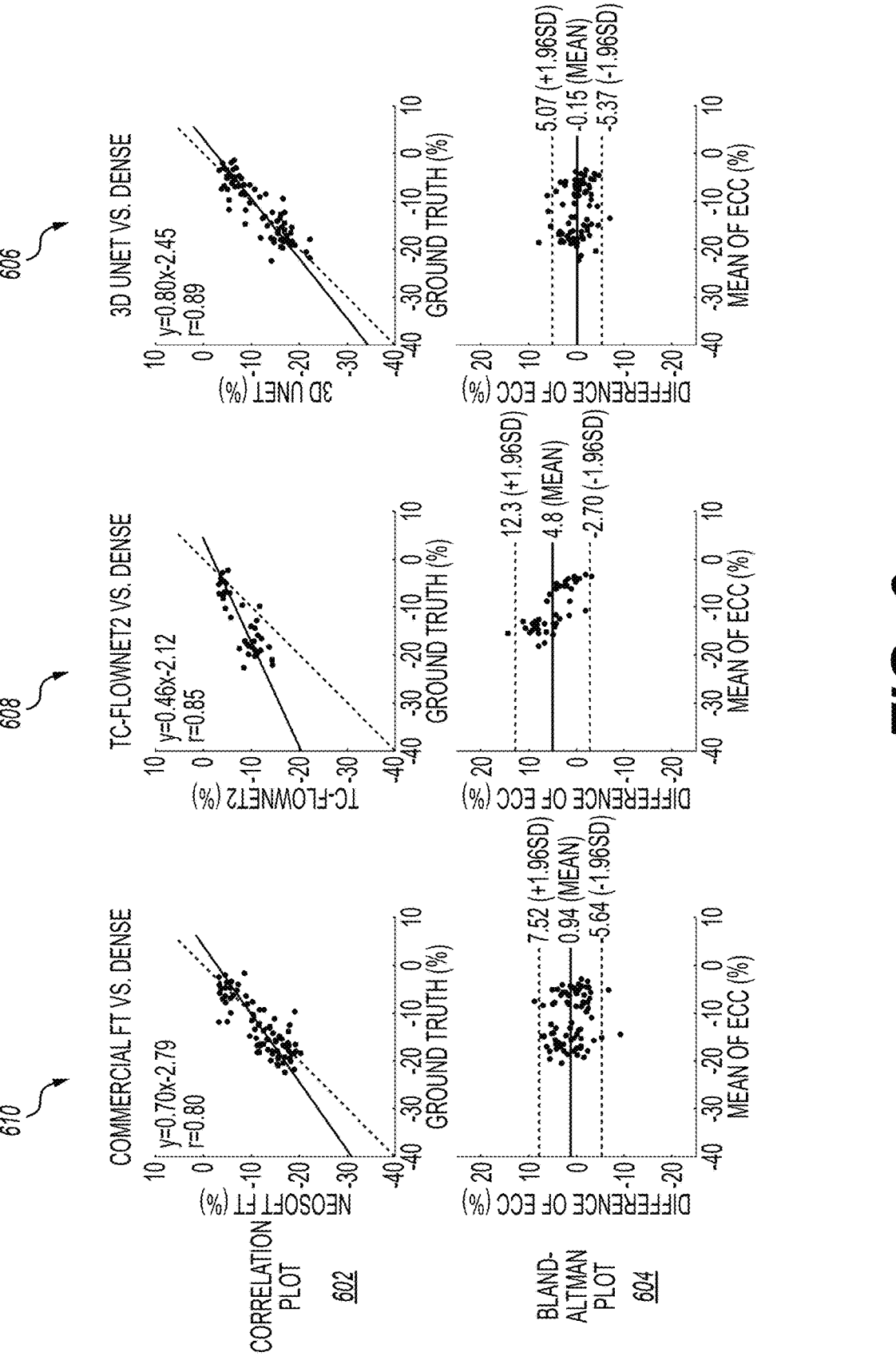
FIG. 6 shows correlation plots and Bland-Altman plots in the estimation of global $E_{cc}$ and segmental $E_{cc}$ data using (i) the 3D-UNet trained using DENSE contour data objects, (ii) the TC-FlowNet2 neural network, and a commercial FT system in accordance with an illustrative embodiment.

Various aspects of the disclosed technology may still be more fully understood from the following description of example implementations and corresponding results and the images of FIGS. 4-6. Some experimental data are presented herein for purposes of illustration and should not be construed as limiting the scope of the disclosed technology in any way or excluding any alternative or additional embodiments.

Figure 4A:
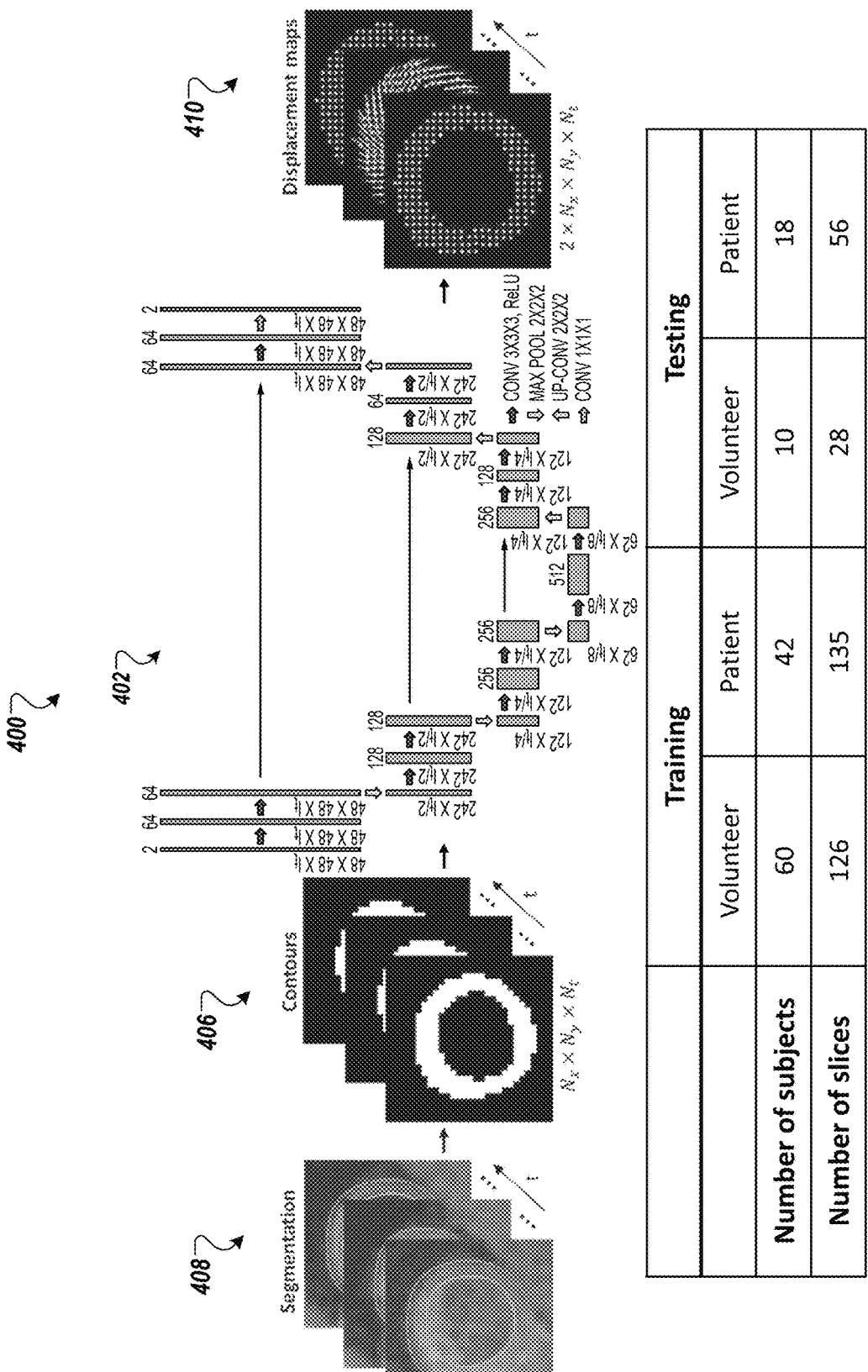
FIG. 4A shows an example method of training a neural network using DENSE MRI training data set in a study in accordance with an illustrative embodiment.

A study was conducted to train a 3D-UNet neural network using DENSE MRI training data set to estimate intramyocardial motion from contour motion. Two workflows were implemented: a two-step FlowNet2-based framework with a through-time correction network and a 3D (2D+t) Unet framework. Both networks depicted cardiac contraction and abnormal motion patterns. The 3D Unet showed excellent reliability for global circumferential strain (Ecc) and good reliability for segmental Ecc, and it outperformed commercial FT for both global and segmental Ecc. FIG. 4A shows an example method of training a neural network using DENSE MRI training data set in a study in accordance with an illustrative embodiment.

Methods (3D Unet). In the study, the 3D-UNet neural network as a 3D convolutional neural network (CNN) 102b (in this figure shown as 402) with an encoder-decoder structure was configured and trained to estimate intramyocardial displacement 116 (shown as 404) from contour motion data objects 108 (shown as 406). The contour motion data objects 406 included a set of time series data having myocardial contour objects derived from DENSE magnitude images 112 (shown as 408). The ground truth data 120 (not shown) included data from DENSE tissue displacement measurements derived from DENSE phase images. Because the DENSE and cine images at matched slice locations share similar motion patterns, the study validated the trained neural network model using contour data derived from the standard cine images.

Figure 4B:
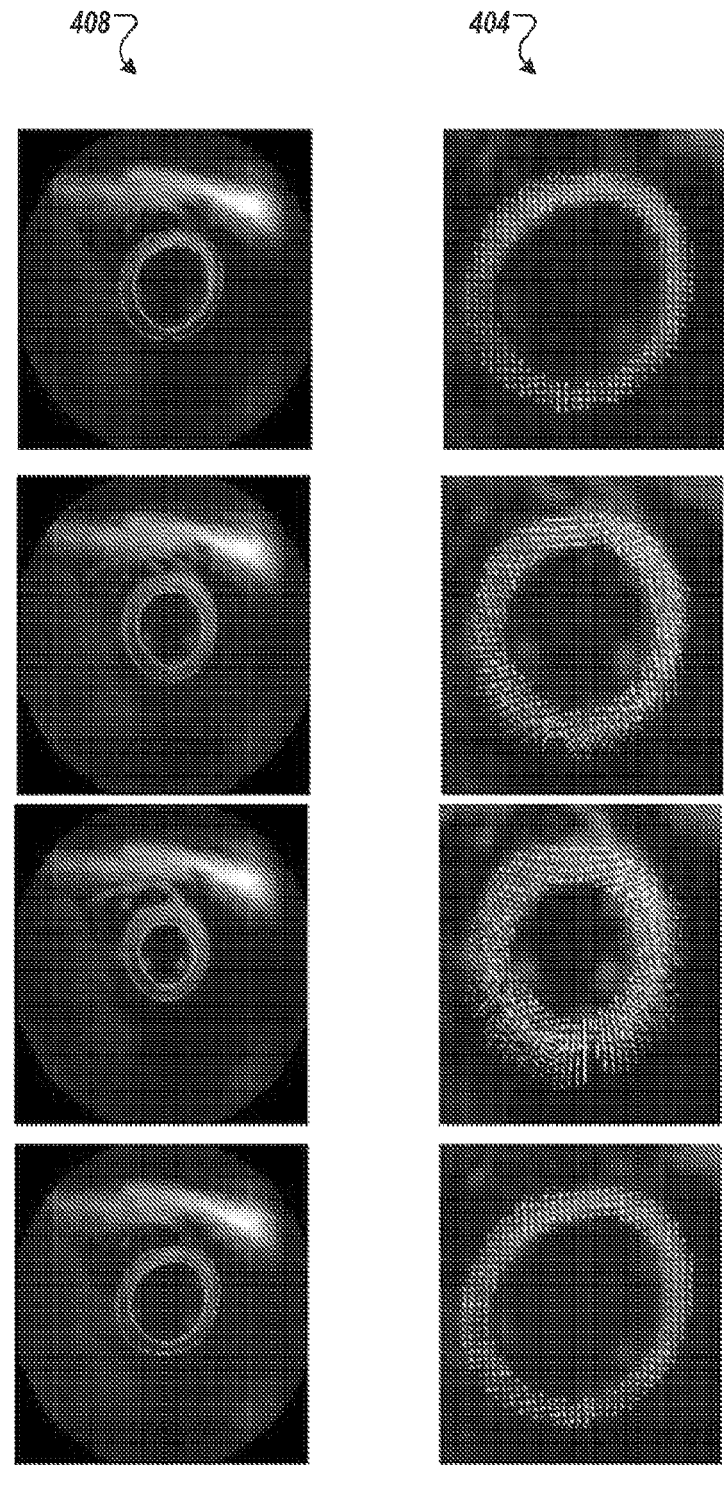
FIGS. 4B-4H show performance results and outputs of the method of training a neural network using DENSE MRI training data set in the study in accordance with an illustrative embodiment.

FIG. 4B shows example inputs of the 3D-Unet neural network 402. FIG. 4B show a sequence of myocardial contour objects derived from DENSE magnitude images 408. FIG. 4B also shows a sequence of the corresponding output intramyocardial displacement 404.

Figure 4C:
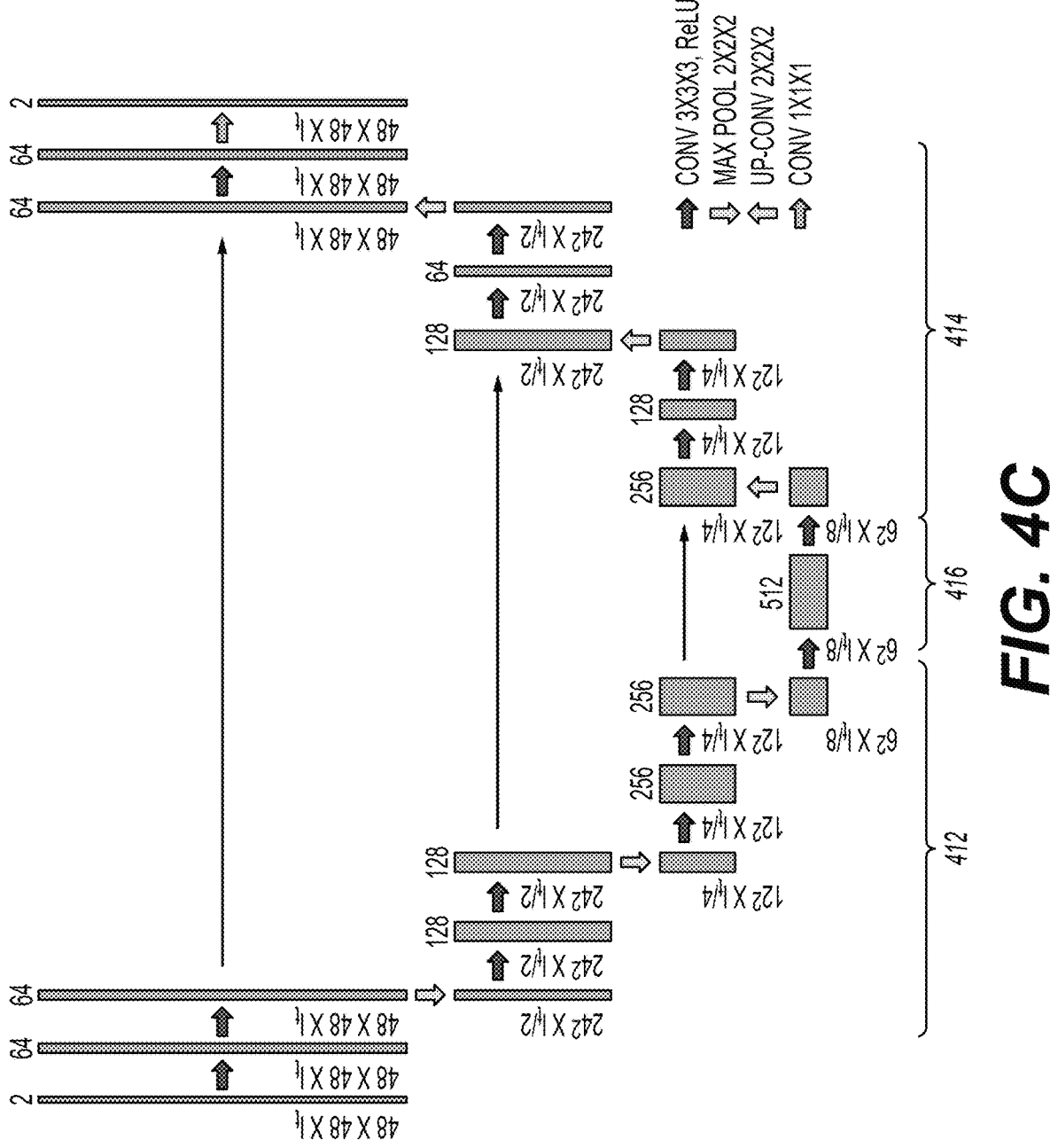

FIG. 4C shows the configuration of a 3D-Unet neural network 402 that was employed in the study. The 3D-Unet neural network 402 includes a CNN that is adapted for 3D image segmentation. The 3D-UNet neural network includes a contractive path 412 and an expanding path 414 and is connected to a centermost part 416 comprising a combination of convolution and pooling operations. After this center part, the image is reconstructed through a combination of convolutions and up-sampling layers. Skip connections are employed to assist with backward flow of gradients during the training.

A 3D UNet architecture included convolution, batch normalization, ReLU layers, residual connections, and pooling layers. The depth of the network that was employed in the study was 3, and the amount of filters used was 64, 128, 256 and 512, from top to bottom level, respectively. The kernel size for the convolution layers was 3*3*3, and the kernel size for the pooling layers was 4*4*2.

The study also evaluated a two-step FlowNet2-based framework with a through-time correction network (TC-FlowNet2). The input size for the FlowNet2-based network was two frames of endocardial and epicardial contours, and the output of the DT-FlowNet2 was the frame-to-frame displacement field. The input of the through-time correction network was a stack of sequential displacements fields from DT-FlowNet2 with a size of $2*N_x*N_y*N_t$, where the factor of 2 accounts for displacements in two directions and $N_t$ represents the number of temporal frames. The output was also a size of $2*N_x*N_y*N_t$. For the 3D-UNet, the input size was $N_x*N_y*N_t$, and the output size was $2*N_x*N_y*N_t$.

Data pre-processing: To prepare the DENSE and cine images for the training and validation operation, the training and validation data set comprising the left ventricular portion of DENSE and cine images were segmented by via binarization operation that fill the myocardium area with a value of "1" and the outside area and blood pool with a value of "0". The images were cropped to a fixed size: $N_x \times N_y$, (e.g., 48*48 pixels to include the full left ventricle region). Data augmentation was performed using a 90° rotation. Cine images (validation data set) were scaled to match the resolution range of DENSE training images and also cropped into 48*48 pixels. Cine images were scaled to match the resolution range of DENSE images. The neural network is configured with an input size of $N_x \times N_y \times N_t$ (e.g., 48*48*$N_t$), in which $N_t$ represents the number of temporal frames and the output size is set as $2 \times N_x \times N_y \times N_t$ (e.g., $2*48*48*N_t$) in which the factor of 2 accounts for the displacements in two directions.

Training. 5-fold cross-validation was applied to the training datasets. The model was trained with the Adam optimizer and a total of 300 epochs. The initial learning rate was set to 1e–4, with a halving schedule for each 100 epochs. The training used the end-point error as the loss function.

Datasets: The study trained the neural network using DENSE training datasets according to the table of FIG. 4A. The training data set included (i) data from 60 volunteers and (ii) data from 42 patients with various pathologies such as left bundle branch block (LBBB), hypertrophic cardiomyopathy, dilated cardiomyopathy, infarction, coronary artery disease and hypertension. The trained neural network model was validated on cine images of 10 volunteers and 18 patients in 3 short-axis views (base, mid-level, and apex). For the TC-FlowNet2 portion of the study, the datasets were divided into two parts to separately train DENSE-trained FlowNet2 and the correction network, thus the testing dataset number (15 subjects, 48 slices) was half the size as that used for the 3D Unet. Commercial feature-tracking (suiteHEART, Neosoft, WI) was also used to measure strain from cine images.

Figure 4D:
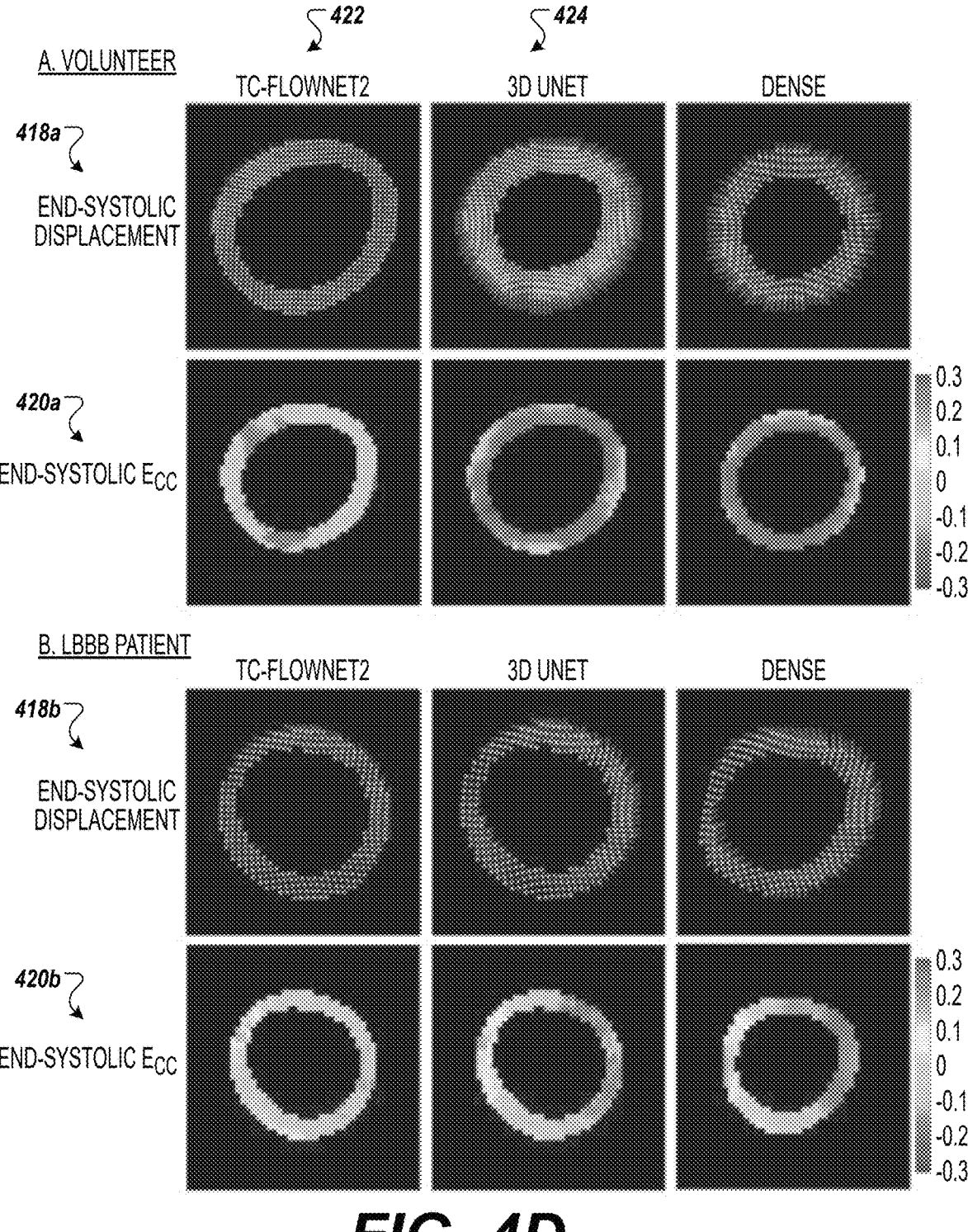

Results: FIG. 4D shows examples results of the TC-FlowNet2, 3D Unet, and DENSE ground truth images for computing end-systolic displacement 418 (shown as 418, 418*b*, respectively) and circumferential strain ($E_{cc}$) 420 (shown as 420*a*, 420*b*, respectively) for a healthy subject and an LBBB patient. In these examples, both neural networks (3D-UNet and TC-FlowNet2) (422, 424) are observed to successfully detect cardiac contraction in the healthy volunteer and the stretching of the septum in the LBBB patient, though the 3D-Unet outputs showed a higher degree of contraction, indicating higher sensitivity.

Figure 4E:
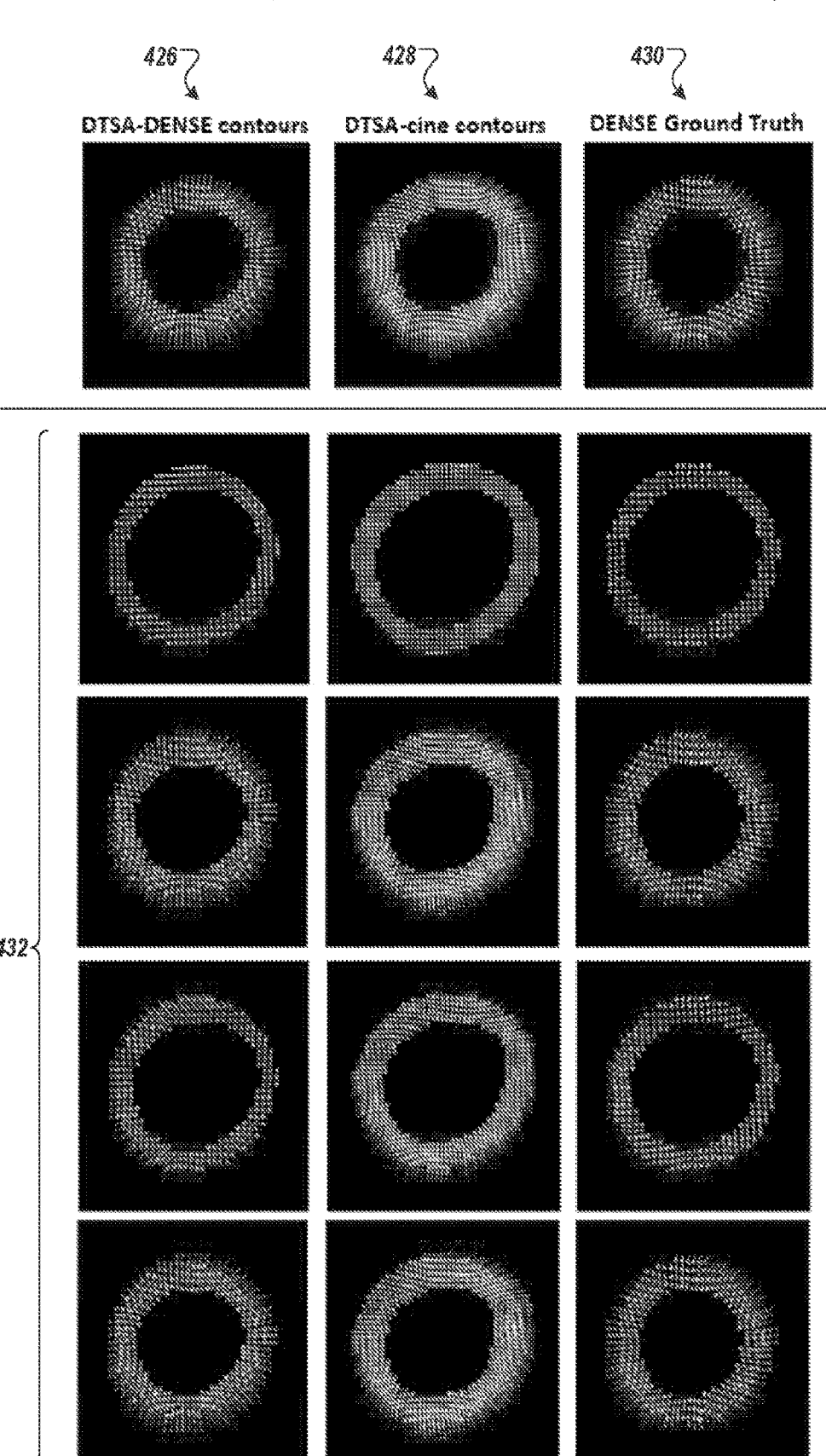
Figure 4F:
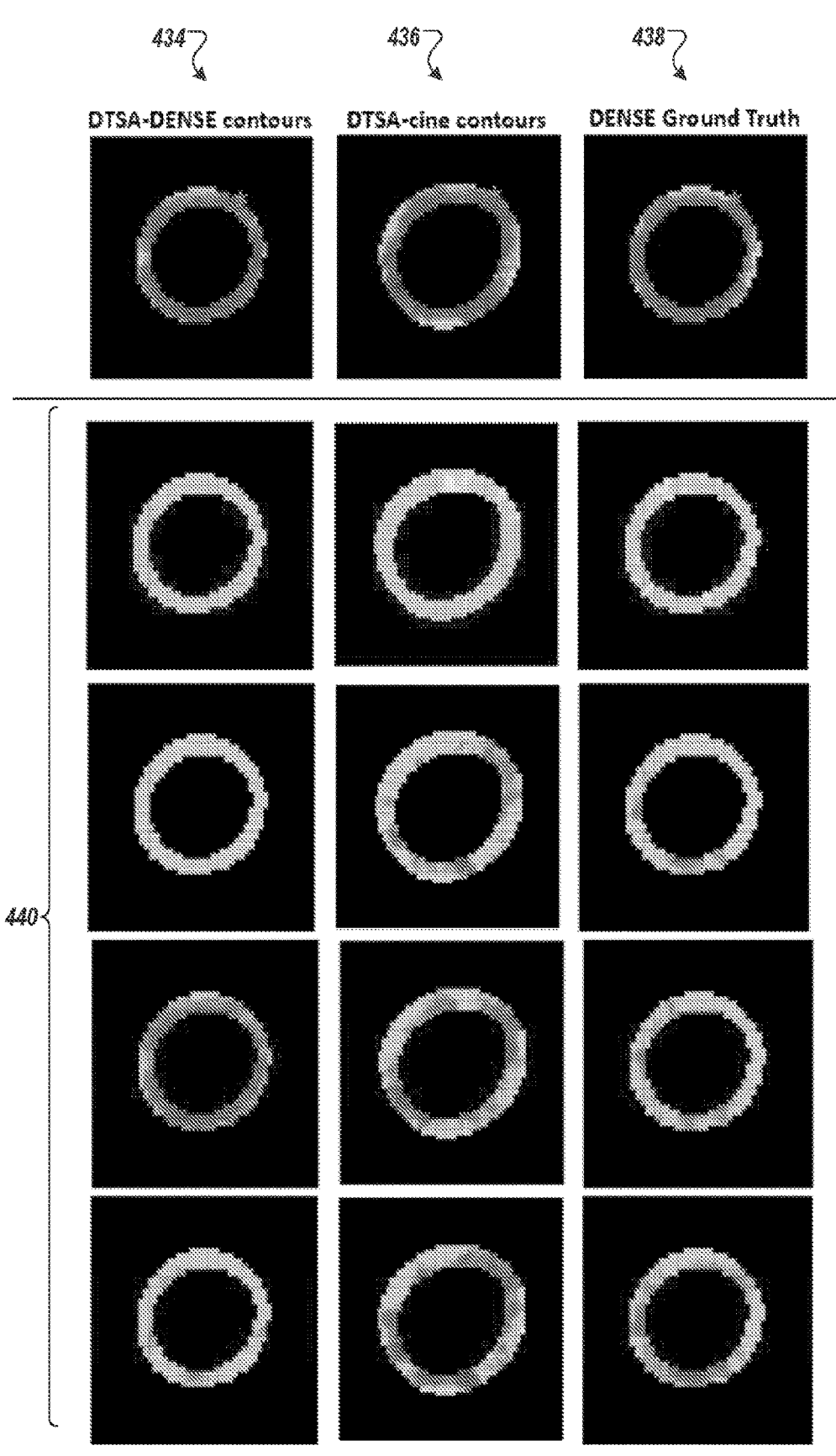

FIG. 4E shows the end-diastolic displacement maps from the 3D-UNet neural network of a volunteer data set (healthy) trained using the DENSE contour data objects 108 (shown as 426) and using cine derived contour data objects 428. The DENSE ground-truth displacement data 120*a* (shown as 430) is shown as comparison. FIG. 4E also shows a sequence 432 of displacement maps generated from the same. It can be observed from the end-diastolic displacement maps and displacement map sequences that both DENSE trained 3D-Unet neural network can provide normal cardiac contraction and show good agreement with DENSE ground truth, though training using the DENSE contour data objects 108 appears to have provided results having a better agreement with the DENSE ground truth data.

FIG. 4E shows the end-diastolic circumferential strain ($E_{cc}$) maps from the 3D-UNet neural network of a volunteer data set (healthy) trained using the DENSE contour data objects 108 (shown as 434) and using cine derived contour data objects 436. The DENSE ground-truth displacement data 120*a* (shown as 438) are shown as a comparison. FIG.

4E also shows a sequence 440 of circumferential strain maps generated from the same. It can be observed from the end-diastolic displacement maps and displacement map sequences that both DENSE trained 3D-Unet neural network can provide normal cardiac contraction and show good agreement with DENSE ground truth, though training using the DENSE contour data objects 108 appears to provide results having a better agreement with the DENSE ground truth data.

Figure 4G:
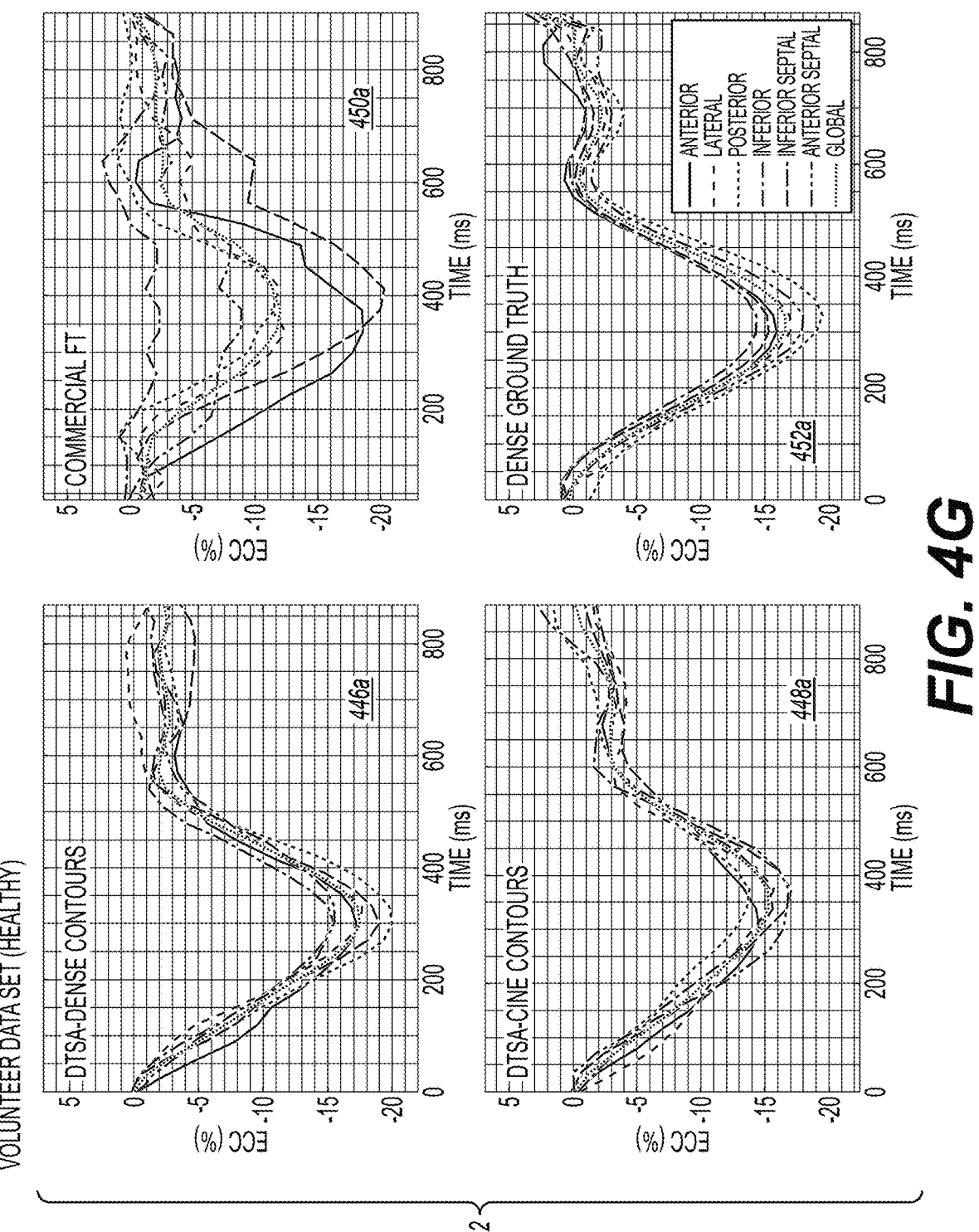
Figure 4H:
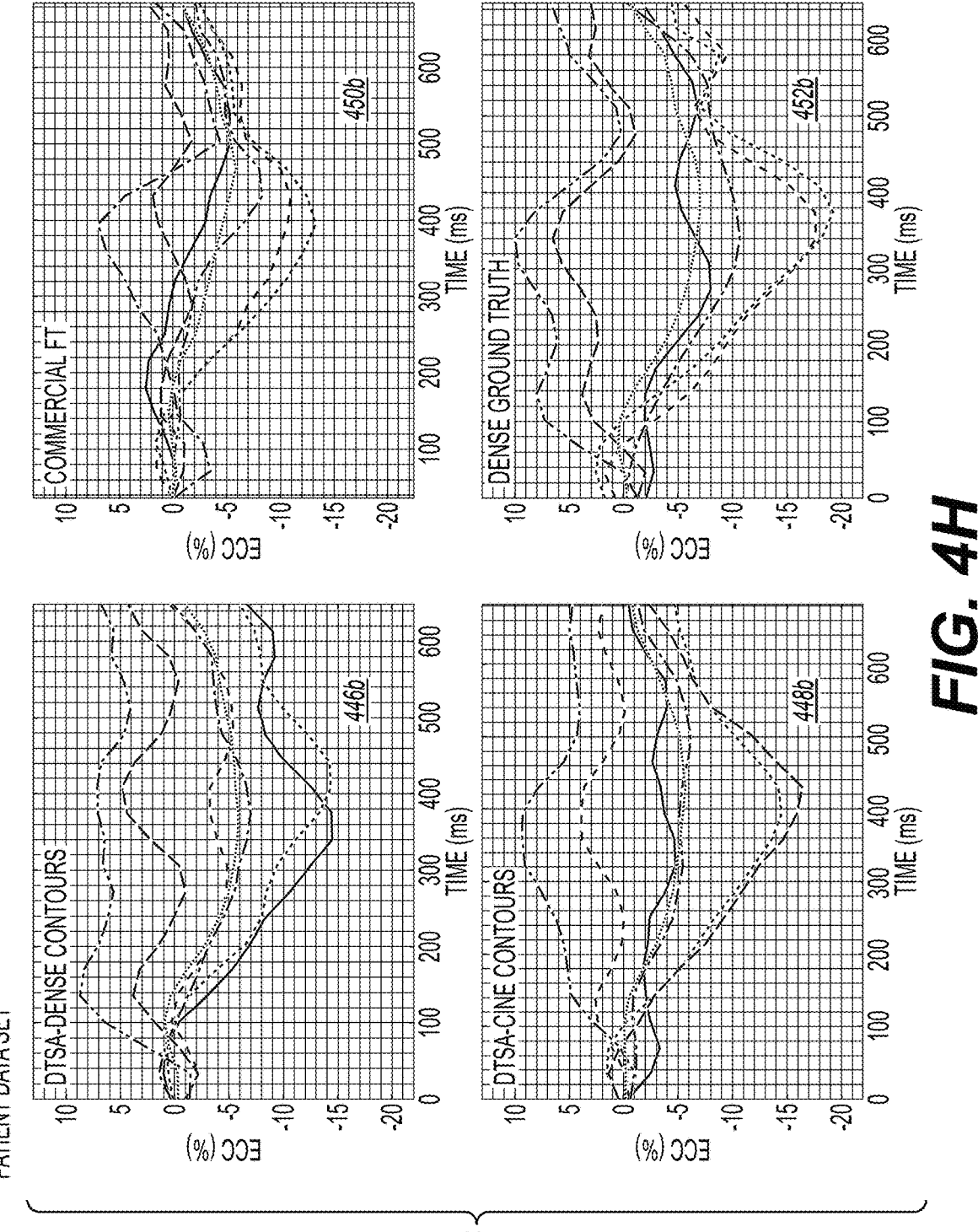

FIGS. 4G and 4H respectively show a comparison of a strain-time curve between the data set of a volunteer (442) and patient (444) using the 3D-UNet neural network trained using the DENSE contour data objects 108 (shown as 446*a*, 446*b*) and the cine contour data objects (448*a*, 448*b*). The outputs of the same data set for a commercial FT system (450*a*, 450*b*) and the DENSE ground truth data (452*a*, 452*b*) are also shown.

From FIGS. 4G and 4H, it can be observed that the two DTSA results (446*a*, 448*a*, 446*b*, 448*b*) are similar to DENSE ground truth (452*a*, 452*b*) for both global and six segmental strains estimation. The commercial FT (450*a*, 450*b*) results do not appear to be aligned to the DENSE ground truth (452*a*, 452*b*).

FIGS. 5A and 5B respectively show correlation plots (502*a*, 502*b*) and Bland-Altman plots (504*a*, 504*b*) in the estimation of global $E_{cc}$ and segmental $E_{cc}$ data using the DENSE contour data objects 108 (shown as 506*a*, 506*b*) and the cine contour data objects (508*a*, 508*b*). In the analysis, Lagragian strain computation were used in which $\epsilon_L = \Sigma \Delta L / L_0$ and the same equation is used for global and segmental $E_{cc}$. The results are shown in comparison to that of a commercial FT system (510*a*, 510*b*). From FIGS. 5A and 5B, it can be observed that the 3D UNet neural network trained using DENSE contour data objects 108 outperformed that trained using cine contour data objects 108 and commercial FT for global and segmental $E_{cc}$ estimation.

FIG. 6 shows correlation plots (602) and Bland-Altman plots (604) in the estimation of global $E_{cc}$ and segmental $E_{cc}$ data using (i) the 3D-UNet trained using DENSE contour data objects (shown as 606), (ii) the TC-FlowNet2 neural network (608), and a commercial FT system (610). From FIG. 6, it can be observed that the 3D-UNet neural network trained using DENSE contour data objects 108 (606) outperformed the commercial FT system and the TC-FlowNet2 neural network for global and segmental $E_{cc}$ estimation.

Table 1 shows the intraclass correlation coefficient (ICC), coefficient of variation (CoV), and Pearson correlation coefficient (Pearson CC) of the use of a commercial FT, TC-FLowNet2 neural network, and the 3D-UNet neural network to estimate global Ecc and segmental Ecc. From Table 1, it can be observed that the 3D-UNet neural network provides the best agreement with the DENSE ground truth data in which the 3D Unet achieved ICC=0.89 for global $E_{cc}$ and ICC=0.75 for segmental $E_{cc}$. Although TC-FlowNet2 showed a good linearity relationship with DENSE, it also seemed to have a relatively big bias, leading to its high Pearson CC but relatively low ICC.

TABLE 1

| Method | Global Ecc | | | Segmental Ecc | | |
| --- | --- | --- | --- | --- | --- | --- |
| | Commercial FT | TC-FlowNet2 | 3D Unet | Commercial FT | TC-FlowNet2 | 3D Unet |
| ICC | 0.78 | 0.49 | 0.89 | 0.54 | 0.41 | 0.75 |
| CoV | 24.13 | 37.08 | 21.64 | 43.35 | 53.06 | 34.43 |
| Pearson CC | 0.80 | 0.85 | 0.89 | 0.55 | 0.68 | 0.76 |

In Table 1, for ICC and Pearson CC, the reliability values can have a range between "0" and "1" in which "1" represents the strongest reliability, values >0.9 indicate excellent reliability, values between 0.75 and 0.9 indicate good reliability, values between 0.5 and 0.75 indicate moderate reliability, and values <0.5 indicates poor reliability. For CoV, the higher the coefficient of variation, the greater the level of dispersion around the mean.

Discussion

Cardiac magnetic resonance (CMR) myocardial strain imaging (also referred to as "strain MRI") is used diagnostically and prognostically for many types of heart disease [6]. Feature tracking (FT) is a widely used and convenient method for strain MRI, as it applies post-processing algorithms directly to standard cine images to assess strain. It is, however, less accurate than strain-dedicated acquisitions like displacement encoding with stimulated echoes (DENSE) (1-4), especially for segmental strain. FT methods track myocardial contours rather than intramyocardial tissue because the myocardium presents uniform signal on cine MRI, lacking features to track. The intramyocardial motion is then (imperfectly) estimated using optical-flow-based methods applied to the times series of endocardial and epicardial contours (5).

In contrast, DENSE directly measures intramyocardial tissue displacement; however, it requires additional acquisitions. As DENSE provides both myocardial contours and accurate intramyocardial tissue displacement information, we investigated the use of DENSE data to train deep networks to predict intramyocardial tissue motion from contour motion. This deep learning (DL) approach may provide the clinical convenience of FT and accuracy similar to DENSE.

A 3D Unet, trained using DENSE datasets to predict intramyocardial motion from contour motion, outperformed both TC-FlowNet2 and commercial FT for the measurement of both global and segmental $E_{cc}$, for which DENSE data at matched locations served the reference standard. The proposed DTSA network showed the ability to depict detailed intramyocardial motion, which is challenging for optical-flow-based FT methods. The proposed network showed improved performance for both global and segmental $E_{cc}$ compared to commercial FT results.

Example MRI System

Figure 7:
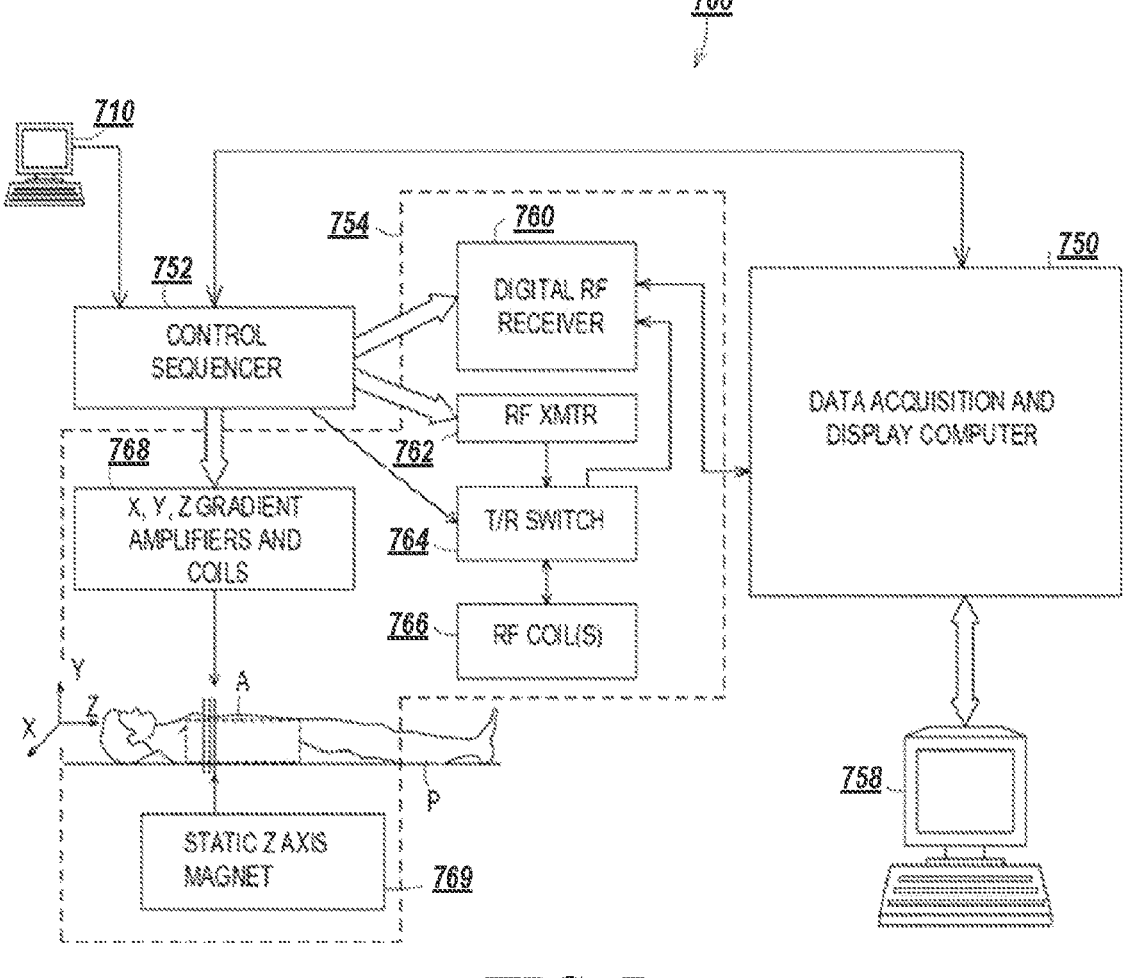
FIG. 7 illustrates an example of a magnetic resonance imaging (MRI) system in accordance with an illustrative embodiment.

FIG. 7 illustrates an example of a magnetic resonance imaging (MRI) system 700, including a data acquisition and display computer 750 coupled to an operator console 710, an MRI real-time control sequencer 752, and an MRI subsystem 754. The MRI subsystem 754 may include XYZ magnetic gradient coils and associated amplifiers 768, a static Z-axis magnet 769, a digital RF transmitter 762, a digital RF receiver 760, a transmit/receive switch 764, and RF coil(s) 766. The MRI subsystem 754 may be controlled in real-time by control sequencer 752 to generate magnetic and radio frequency fields that stimulate magnetic resonance phenomena in a living subject, patient P, to be imaged. A contrast-enhanced image of an area of interest A of the patient P may be shown on display 758. The display 758 may be implemented through a variety of output interfaces, including a monitor, printer, or data storage.

The area of interest "A" corresponds to a region associated with one or more physiological activities in patient "P". The area of interest shown in the example embodiment of FIG. 7 corresponds to a chest region of patient "P", but the area of interest for purposes of implementing aspects of the disclosure presented herein is not limited to the chest area. It should be recognized and appreciated that the area of interest can be one or more of a brain region, heart region, and upper or lower limb regions of the patient "P", for example. Physiological activities that may be analyzed by methods and systems in accordance with various embodiments of the present disclosure may include, but are not limited to, muscular movement or fluid flow in particular areas of interest.

It should be appreciated that any number and type of computer-based medical imaging systems or components, including various types of commercially available medical imaging systems and components, may be used to practice certain aspects of the present disclosure. Systems, as described herein with respect to example embodiments, are not intended to be specifically limited to magnetic resonance imaging (MRI) implementations or the particular system shown in FIG. 7.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Example Computing Environment and System

Figure 8:
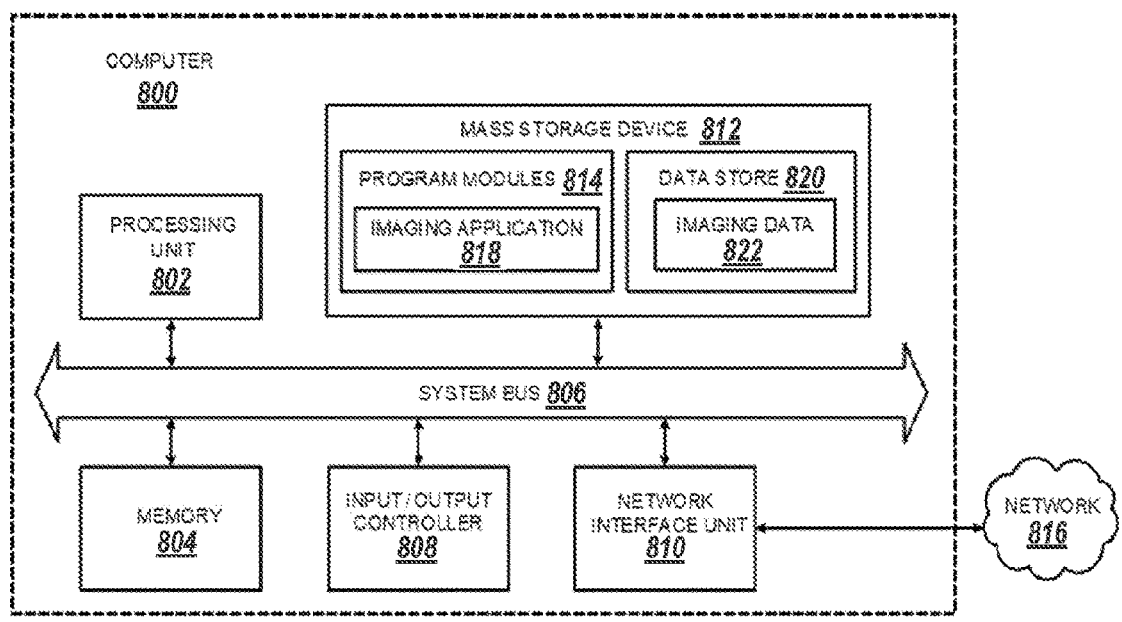
FIG. 8 is a computer architecture diagram showing a computing system capable of implementing aspects of the present disclosure in accordance with one or more embodiments described herein.

FIG. 8 is a computer architecture diagram showing a computing system capable of implementing aspects of the present disclosure in accordance with one or more embodiments described herein. A computer 800 may be configured to perform one or more functions associated with embodiments of intramyocardial motion and/or measurand analysis using a neural network illustrated in one or more of FIGS. 1-6. For example, the computer 800 may be configured to perform operations of the method shown in FIG. 1 and as described above. It should be appreciated that the computer 800 may be implemented within a single computing device or a computing system formed with multiple connected computing devices. The computer 800 may be configured to perform various distributed computing tasks, which may distribute processing and/or storage resources among the multiple devices. The data acquisition and display computer 150 and/or operator console 110 of the system shown in FIG. 1 may include one or more systems and components of the computer 800.

As shown, the computer 800 includes a processing unit 802 ("CPU"), a system memory 804, and a system bus 806 that couples the memory 804 to the CPU 802. The computer 800 further includes a mass storage device 812 for storing program modules 814. The program modules 814 may be operable to perform one or more functions associated with embodiments of the method as illustrated in one or more of FIGS. 1-6 discussed above, for example, to cause the computer 800 to perform operations of the intramyocardial motion and/or measurand analysis using a neural network shown in FIG. 1 and as described above. The program modules 814 may include an imaging application 818 for performing data acquisition functions as described herein, for example, to receive image data corresponding to magnetic resonance imaging of an area of interest. The computer 800 can include a data store 820 for storing data that may include imaging-related data 822 such as acquired image data, and a modeling data store 824 for storing image modeling data, or other various types of data utilized in practicing aspects of the present disclosure.

The mass storage device 812 is connected to the CPU 802 through a mass storage controller (not shown) connected to the bus 806. The mass storage device 812 and its associated computer-storage media provide non-volatile storage for the computer 800. Although the description of computer-storage media contained herein refers to a mass storage device, such as a hard disk or CD-ROM drive, it should be appreciated by those skilled in the art that computer-storage media can be any available computer storage media that can be accessed by the computer 800.

By way of example, and not limitation, computer-storage media (also referred to herein as a "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid-state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 800. Transitory signals are not "computer-storage media", "computer-readable storage medium" or "computer-readable storage media" as described herein.

According to various embodiments, the computer 800 may operate in a networked environment using connections to other local or remote computers through a network 816 via a network interface unit 810 connected to the bus 806. The network interface unit 810 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 800 may also include an input/output controller 808 for receiving and processing input from a number of input devices. Input devices may include one or more keyboards, mice, stylus, touchscreens, microphones, audio capturing devices, or image/video capture devices. An end-user may utilize such input devices to interact with a user interface, for example, a graphical user interface, for managing various functions performed by the computer 800.

The bus 806 may enable the processing unit 802 to read code and/or data to/from the mass storage device 812 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state or may include rotating media storing magnetically-encoded information. The program modules 814, which include the imaging application 818, may include instructions that, when loaded into the processing unit 802 and executed, cause the computer 800 to provide functions associated with embodiments illustrated in FIGS. 3-14. The program modules 814 may also provide various tools or techniques by which the computer 800 may participate within the overall systems or operating environments using the components, flows, and data structures discussed throughout this description.

In general, the program modules 814 may, when loaded into the processing unit 802 and executed, transform the processing unit 802 and the overall computer 800 from a general-purpose computing system into a special-purpose computing system. The processing unit 802 may be constructed from any number of transistors or other discrete circuit elements, which may individually or collectively assume any number of states. More specifically, the processing unit 802 may operate as a finite-state machine, in response to executable instructions contained within the program modules 814. These computer-executable instructions may transform the processing unit 802 by specifying how the processing unit 802 transitions between states, thereby transforming the transistors or other discrete hardware elements constituting the processing unit 802.

Encoding the program modules 814 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer-storage media are implemented as semiconductor-based memory, the program modules 814 may transform the physical state of the semiconductor memory, when the software is encoded therein. For example, the program modules 814 may transform the state of transistors, capacitors, or other discrete circuit elements constituting the semiconductor memory.

As another example, the computer-storage media may be implemented using magnetic or optical technology. In such implementations, the program modules 814 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

LIST OF REFERENCES

[1] Wehner G J, Jing L, Haggerty C M, Suever J D, Chen J, Hamlet S M, Feindt J A, Mojsejenko W D, Fogel M A, Fornwalt B K. Comparison of left ventricular strains and torsion derived from feature tracking and DENSE CMR. Journal of Cardiovascular Magnetic Resonance. 2018 December; 20(1):1-1.

[2] Lin K, Meng L, Collins J D, Chowdhary V, Markl M, Carr J C. Reproducibility of cine displacement encoding with stimulated echoes (DENSE) in human subjects. Magn Reson Imaging. 2017; 35:148-53.

[3] Bilchick K C, Auger D A, Abdishektaei M, Mathew R, Sohn M W, Cai X, et al. CMR DENSE and the Seattle Heart Failure Model Inform Survival and Arrhythmia Risk After CRT. JACC Cardiovasc Imaging. 2020; 13(4): 924-36.

[4] Mangion K, Loughrey C M, Auger D A, McComb C, Lee M M, Corcoran D, et al. Displacement Encoding With Stimulated Echoes Enables the Identification of Infarct Transmurality Early Postmyocardial Infarction. J Magn Reson Imaging. 2020; 52(6):1722-31.

[5] Schuster A, Hor K N, Kowallick J T, Beerbaum P, Kutty S. Cardiovascular Magnetic Resonance Myocardial Feature Tracking: Concepts and Clinical Applications. Circ Cardiovasc Imaging. 2016; 9(4):e004077.

[6] Scatteia, A., Baritussio, A. & Bucciarelli-Ducci, C, "Strain imaging using cardiac magnetic resonance," Heart Fail Rev 22, 465-476 (2017).

[7] Simpson, R. M. et al., JMRI 2013; 37(3): 576-599.

[8] Spottiswoode, B. S. et al., Med. Image Anal. 2009, 13:105-15.

[9] Young, A. A. et al., Magnetic Resonance in Medicine 2012, 67(6): 1590-1599.

[10] Spottiswoode, B. S. et al, IEEE Trans. Med. Imaging 2007; 26:15-20.

[11] Gilliam, A. D. et al., IEEE Trans. Med. Imaging 2012, 31:1669-81.

[12] Xu, W. et al., IEEE Trans. on Geoscience and Remote Sensing 1999, 37:124-34.

What is claimed is:

1. A method of determining intramyocardial motion and/or measurand in medical image scans, the method comprising:

retrieving, by a processor, a medical image scan of a subject;

determining, by the processor, intramyocardial motion data in the medical image scan, in part, using a trained neural network, wherein the trained neural network has been trained by:

(i) generating a set of contour motion images or data from Displacement-ENcoding with Stimulated Echoes (DENSE) magnitude images or data and a set of training displacement map images or data from DENSE phase images or data; and (ii) configuring a neural network comprising an input and output to generate the trained neural network by (a) applying the set of contour motion images or data to the input to generate an output displacement map image or data and (b) applying the set of the training displacement map images or data, or parameters derived therefrom, to the output displacement map to adjust weights of the neural network;

wherein the determined intramyocardial motion data, or a parameter derived therefrom, is outputted in a report or employed in a control operation for the diagnostics or treatment of cardiac disease or cardiac health-related conditions.

2. The method of claim 1, wherein the medical image scan is at least one of: cardiac computer tomography (CT) images, magnetic resonance imaging (MRI) images, echocardiogram images, and heart ultrasound images.

3. The method of claim 1 further comprising:

determining, by the processor, a set of values associated with at least one of a strain parameter, a strain rate parameter, a torsion parameter, and a twist parameter using the determined intramyocardial motion data, wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

4. The method of claim 1, wherein the set of contour motion images or data is generated by:

binarizing pixels of the DENSE magnitude images or data to a binary value corresponding to contour motions defined within the DENSE magnitude images or data.

5. The method of claim 4, wherein the set of contour motion images or data is further generated by:

scaling the DENSE magnitude images or data to a predefined image size; and cropping the scaled DENSE magnitude images or data to an image region of interest.

6. The method of claim 1, wherein the neural network comprises a convolutional neural network comprising one or more convolution layers, one or more batch normalization layers, one or more ReLU layers, and one or more pooling layers, the layers being connected together collectively to form a network.

7. The method of claim 1, wherein the neural network comprises a 3D UNet neural network.

8. The method of claim 1, wherein the DENSE magnitude images or data and the DENSE phase images or data are determined from a plurality of DENSE training data sets, wherein the plurality of DENSE training data sets are acquired by:

acquiring first data comprising a stimulated echo and a Tl relaxation echo;

acquiring second data comprised of a second stimulated echo, a second Tl relaxation echo, and a second stimulated anti-echo;

acquiring at least one of original frames comprising the stimulated echo and the Tl relaxation echo;

acquiring at least one of additional original frames comprising a stimulated echo, a Tl relaxation echo, and a stimulated anti-echo; and acquiring a plurality of new original frames of displacement encoded stimulated echo (DENSE) cine frames of MRI image data of a subject.

9. A method of training a neural network having an input and output to generate an output displacement map corresponding to intramyocardial motion in a biomedical image, the method comprising:

generating, via a processor, a set of contour motion images or data from DENSE magnitude images or data;

generating, via the processor, a set of training displacement map images or data from DENSE phase images or data; and configuring the neural network by (i) applying the set of contour motion images or data to the input of the neural network to generate an output displacement map image or data and (ii) applying the set of training displacement map images or data, or parameter derived therefrom, to the output displacement map to adjust weights of the neural network, wherein the trained neural network is employed to determine intramyocardial motion data, or a parameter derived therefrom, and wherein output of the trained neural network is outputted in a report or employed in a control operation for the diagnostics or treatment of cardiac disease or cardiac health-related conditions.

10. The method of claim 9, wherein the medical image scan is at least one of: cardiac computer tomography (CT) images, magnetic resonance imaging (MRI) images, echocardiogram images, heart ultrasound images.

11. The method of claim 9, wherein the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

12. The method of claim 9, wherein the set of contour motion images or data is generated by:

scaling the DENSE magnitude images or data to a pre-defined image size;

cropping the scaled DENSE magnitude images or data to an image region of interest; and binarizing pixels of the DENSE magnitude images or data to a binary value corresponding to contour motions defined within the DENSE magnitude images or data.

13. A system comprising:

a processor; and a memory having instructions stored thereon to determine intramyocardial motion and/or measurand in medical image scans, wherein execution of the instructions by the processor causes the processor to:

retrieve medical image scan of a subject;

determine intramyocardial motion data in the medical image scan, in part, using a trained neural network, wherein the trained neural network has been trained by:

(i) generating a set of contour motion images or data from Displacement-ENcoding with Stimulated Echoes (DENSE) magnitude images or data and a set of training displacement map images or data from DENSE phase images or data; and (ii) configuring a neural network comprising an input and output to generate the trained neural network by (a) applying the set of contour motion images or data to the input to generate an output displacement map image or data and (b) applying the set of training displacement map images or data to the output displacement map to adjust weights of the neural network;

wherein the determined intramyocardial motion data, or a parameter derived therefrom, is outputted in a report or employed in a control operation for the diagnostics or treatment of cardiac disease or cardiac health-related conditions.

14. The system of claim 13, wherein the medical image scan is at least one of: cardiac computer tomography (CT) images, magnetic resonance imaging (MRI) images, echocardiogram images, and heart ultrasound images.

15. The system of claim 13, wherein the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

16. The system of claim 13, wherein the instructions include:

a first instruction to scale the DENSE magnitude images or data to a pre-defined image size;

a second instruction to crop the scaled DENSE magnitude images or data to an image region of interest; and a third instruction to binarize pixels of the DENSE magnitude images or data to a binary value corresponding to contour motions defined within the DENSE magnitude images or data.

17. A non-transitory computer-readable medium having instructions stored thereon to determine intramyocardial motion and/or measurand in medical image scans, wherein execution of the instructions by the processor causes the processor to:

retrieve medical image scan of a subject;

determine intramyocardial motion data in the medical image scan, in part, using a trained neural network, wherein the trained neural network has been trained by:

(i) generating a set of contour motion images or data from Displacement-ENcoding with Stimulated Echoes (DENSE) magnitude images or data and a set of training displacement map images or data from DENSE phase images or data; and (ii) configuring a neural network comprising an input and output to generate the trained neural network by (a) applying the set of contour motion images or data to the input to generate an output displacement map image or data and (b) applying the set of training displacement map images or data to the output displacement map to adjust weights of the neural network;

wherein the determined intramyocardial motion data, or a parameter derived therefrom, is outputted in a report or employed in a control operation for the diagnostics or treatment of cardiac disease or cardiac health-related conditions.

18. The non-transitory computer-readable medium of claim 17, wherein the medical image scan is at least one of: cardiac computer tomography (CT) images, magnetic resonance imaging (MRI) images, echocardiogram images, and heart ultrasound images.

19. The non-transitory computer-readable medium of claim 17, wherein the determined intramyocardial motion data is employed to determine a set of values associated with at least one of a strain parameter, a strain rate parameter, a torsion parameter, and a twist parameter, and wherein the determined set of values associated with the at least one of the strain parameter, the strain rate parameter, the torsion parameter, and the twist parameter is outputted in the report or employed in the control operation for the diagnostics or the treatment of cardiac disease or the cardiac health-related conditions.

20. The non-transitory computer-readable medium of claim 17, wherein the instructions include:

a first instruction to scale the DENSE magnitude images or data to a pre-defined image size;

a second instruction to crop the scaled DENSE magnitude images or data to an image region of interest; and a third instruction to binarize pixels of the DENSE magnitude images or data to a binary value corresponding to contour motions defined within the DENSE magnitude images or data.

* * * * *